United States Patent [19]

Webber et al.

[11] Patent Number: 5,741,800
[45] Date of Patent: Apr. 21, 1998

[54] AZOLYL-CYCLIC AMINE DERIVATES WITH IMMUNOMODULATORY ACTIVITY

[75] Inventors: David George Webber; Gerald Bernard Tometzki; Michael Henry Hockley; Roger Bernard Titman; Roy Victor Davies; Paul Anthony Bradley, all of Nottingham, United Kingdom

[73] Assignee: Knoll Aktiengesellachaft, Ludwigshafen, Germany

[21] Appl. No.: 564,155

[22] Filed: Dec. 21, 1995

[30] Foreign Application Priority Data

Jun. 22, 1993 [GB] United Kingdom ............... 9312806

[51] Int. Cl.$^6$ ............ C07D 401/06; C07D 403/06; A61K 31/445
[52] U.S. Cl. ............ 514/322; 514/326; 514/234.2; 514/234.5; 546/210; 546/199; 544/121; 544/129; 544/130
[58] Field of Search ............ 546/199, 210; 514/322, 326

[56] References Cited

U.S. PATENT DOCUMENTS

| | | | |
|---|---|---|---|
| 3,459,757 | 8/1969 | Wright et al. | 546/210 |
| 3,793,317 | 2/1974 | Beaman et al. | 514/398 |
| 4,022,783 | 5/1977 | Shroff et al. | 514/252 |
| 4,241,060 | 12/1980 | Smithen | 514/212 |
| 4,338,453 | 7/1982 | Gall | 544/360 |
| 4,404,382 | 9/1983 | Gall | 544/360 |
| 4,404,387 | 9/1983 | Gall | 544/360 |
| 4,695,575 | 9/1987 | Janssens et al. | 514/322 |
| 4,707,487 | 11/1987 | Arrang et al. | 514/326 |
| 4,906,643 | 3/1990 | Van Deele et al. | 514/318 |
| 4,925,851 | 5/1990 | Houlihan | 514/326 |
| 4,935,417 | 6/1990 | Pascal et al. | 514/218 |
| 5,166,205 | 11/1992 | Cuberes-Altisent et al. | 514/252 |
| 5,175,157 | 12/1992 | Psiorz et al. | 514/213 |
| 5,280,034 | 1/1994 | Hall et al. | 514/374 |
| 5,547,972 | 8/1996 | Clegg et al. | 514/399 |

FOREIGN PATENT DOCUMENTS

| | | |
|---|---|---|
| 029 707 | 6/1981 | European Pat. Off. . |
| 092 391 | 10/1983 | European Pat. Off. . |
| 468 885 | 1/1992 | European Pat. Off. . |
| 92/06082 | 4/1992 | WIPO . |
| 92/10491 | 6/1992 | WIPO . |

OTHER PUBLICATIONS

88–309195/44—English abstract of EP 289 227, Nov. 2, 1988.

88–053934/08—English abstract of JP 63 010 767, Jan. 18, 1988.

Primary Examiner—Mukund J. Shah
Assistant Examiner—King Lit Wong
Attorney, Agent, or Firm—Keil & Weinkauf

[57] ABSTRACT

A compound of the formula (I),

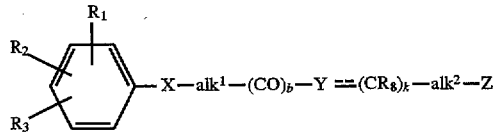

as defined in the specification, having immunomodulatory activity, or a pharmaceutically acceptable salt thereof, pharmaceutical compositions comprising the compound, and processes to make and to use the compound are described.

11 Claims, No Drawings

AZOLYL-CYCLIC AMINE DERIVATES WITH IMMUNOMODULATORY ACTIVITY

This is a 371 application of PCT/EP94/01925 filed Jun. 10, 1994.

The present invention relates to novel therapeutic agents, and in particular to cyclic amines, to processes for their preparation, to pharmaceutical compositions containing them and to their therapeutic activity as immunomodulatory agents. The present invention relates to compounds of formula I

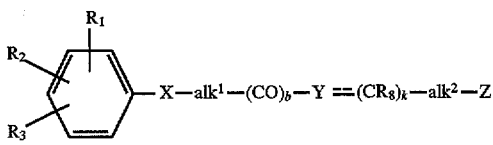

or pharmaceutically acceptable salts thereof, in which $R_1$, $R_2$ and $R_3$ independently represent hydrogen; halo; cyano; hydroxy($C_{1-6}$)alkyl; $C_{1-6}$ alkyl (optionally halogenated); $C_{1-6}$ alkoxy (optionally halogenated); $C_{2-6}$ alkanoyl; $C_{2-6}$ alkoxycarbonyl; $C_{2-6}$alkoxycarbonyl($C_{1-6}$)alkyl; carboxy; nitro; imidazolyl; carboxy($C_{1-6}$)alkyl; $C_{2-6}$alkanoyl($C_{1-6}$)alkyl; $C_{1-6}$alkoxy($C_{1-6}$)alkyl; $NR_{21}R_{22}$; $R_{23}R_{24}N(C_{1-6})$alkyl; $CONR_{25}R_{26}$; $R_{27}R_{28}NCO(C_{1-6})$alkyl; $S(O)_nR_{29}$; a phenyl group, a phenoxy group, or a benzyloxy group; or $R_1$ and $R_2$ together with the phenyl group to which they are attached form a naphthyl group; or $R_1$ together with X and the phenyl group to which they are attached form a tetrahydronaphthyl group; each of said phenyl, phenoxy, benzyloxy, naphthyl or tetrahydronaphthyl groups being optionally substituted by one or more of halo, trifluoromethyl, $C_{1-6}$ alkyl or $C_{1-6}$ alkoxy; $R_{21}$ and $R_{22}$ independently represent hydrogen or $C_{1-6}$ alkyl or $R_{21}$ and $R_{22}$ together with the nitrogen to which they are attached form a 1-pyrrolidinyl group, a morpholino group or a piperidino group; $R_{23}$ and $R_{24}$ independently represent hydrogen or $C_{1-6}$ alkyl or $R_{23}$ and $R_{24}$ together with the nitrogen to which they are attached form a 1-pyrrolidinyl group, a morpholino group or a piperidino group; $R_{25}$ and $R_{26}$ independently represent hydrogen or $C_{1-6}$ alkyl; $R_{27}$ and $R_{28}$ independently represent hydrogen or $C_{1-6}$ alkyl; $R_{29}$ represents $C_{1-6}$ alkyl; h represents 0 or 1;

X represents a bond, a sulphur atom, an oxygen atom, vinylene, carbonyl or —NHCO—;

$alk^1$ represents a $C_{1-6}$ alkylene chain optionally substituted by one or more $C_{1-4}$ alkyl groups;

b represents 0 or 1;

Y represents a saturated 5 or 6 membered heterocyclic ring containing one or two nitrogen atoms, the ring optionally substituted by one or two groups selected from $C_{1-6}$ alkyl, hydroxy($C_{1-6}$)alkyl and ($C_{1-6}$)-alkoxy($C_{1-6}$)alkyl;

$R_8$ represents hydrogen or $C_{1-4}$ alkyl; k represents 0 or 1 provided that when k is 1, $CR_8$ is linked to a carbon atom in the group Y;

the dotted line in ---,
(a) represents a bond when k is 1; or
(b) does not represent a bond when k is 0;

$alk^2$ represents a $C_{1-6}$ alkylene chain optionally substituted by one or more $C_{1-4}$ alkyl groups;

Z represents an aromatic heterocyclic ring system comprising a 5 membered ring selected from imidazolyl, triazolyl and tetrazolyl, each ring being connected to $alk^2$ via a nitrogen atom and each ring optionally having a benzene ring or a pyridine ring fused thereto, the ring system being optionally substituted by one, two or three groups selected from halo; trifluoromethyl; cyano; hydroxy; nitro; $C_{1-12}$ alkyl; $C_{1-6}$ alkoxy; carboxy, carboxy($C_{1-6}$)alkyl; $C_{1-6}$alkoxy($C_{1-6}$)alkyl; $C_{2-6}$alkoxycarbonyl; $C_{2-6}$alkoxycarbonyl($C_{1-6}$)alkyl; $C_{2-6}$alkanoyl; $C_{2-6}$alkanoyl($C_{1-6}$)alkyl; $NR_4R_5$; $R_6R_7N(C_{1-6})$alkyl; $CONR_{16}R_{17}$; $R_{18}R_{19}NCO(C_{1-6})$alkyl; $S(O)_mR_{20}$; a phenyl group optionally substituted by $C_{1-6}$ alkyl, $C_{1-6}$ alkoxy, trifluoromethyl or halo; a benzoyl group optionally substituted by $C_{1-6}$ alkyl, $C_{1-6}$ alkoxy, trifluoromethyl or halo; and a benzyl group optionally substituted by $C_{1-6}$ alkyl, $C_{1-6}$ alkoxy, trifluoromethyl or halo; $R_4$ and $R_5$ independently represent hydrogen or $C_{1-6}$ alkyl or $R_4$ and $R_5$ together with the nitrogen to which they are attached form a 1-pyrrolidinyl group, a morpholino group or a piperidino group; $R_6$ and $R_7$ independently represent hydrogen or $C_{1-6}$ alkyl or $R_6$ and $R_7$ together with the nitrogen to which they are attached form a 1-pyrrolidinyl group, a morpholino group or a piperidino group; $R_{16}$ and $R_{17}$ independently represent hydrogen or $C_{1-6}$ alkyl; $R_{18}$ and $R_{19}$ independently represent hydrogen or $C_{1-6}$ alkyl; $R_{20}$ represents $C_{1-6}$ alkyl; and m represents 0, 1 or 2;

provided that,
(a) when Y is connected to $alk^1$ through a nitrogen atom, b is 0 and X represents a sulphur atom or an oxygen atom, $alk^1$ does not represent methylene;
(b) when k is 0 and Y is connected to $alk^2$ through a nitrogen atom, then $alk^2$ does not represent methylene, and
(c) when X represents carbonyl or —NHCO— then b does not represent 1.

It will be understood that a group containing a chain of 3 or more carbon atoms may be straight or branched, for example propyl includes n-propyl and isopropyl, and butyl includes n-butyl, sec-butyl, isobutyl and tert-butyl. The total number of carbon atoms is specified for certain substituents, for example $C_{2-6}$ alkoxycarbonyl refers to an alkoxycarbonyl group having from two to six carbon atoms. The term "halo" covers fluoro, chloro or bromo.

In compounds of formula I, when $R_1$, $R_2$ and $R_3$ either together or separately represent other than hydrogen, the substituent may replace any hydrogen attached to a carbon atom in the phenyl ring and may be located at any position of the phenyl ring, eg at positions 2, 3 and/or 4. Preferably where at least one of $R_1$, $R_2$ and $R_3$ is other than hydrogen, at least one substituent is located at the 4 position. Preferably, when the groups $R_1$, $R_2$, $R_3$ are phenyl, phenoxy or benzyloxy they are unsubstituted or may be substituted with one or two substituents as hereinabove defined (preferably when said groups include at least one substituent, at least one substituent is located at the 3 or 4 position).

Preferably $R_{21}$, $R_{22}$, $R_{23}$, $R_{24}$, $R_{25}$, $R_{26}$, $R_{27}$ and $R_{28}$ independently represent hydrogen, methyl or ethyl.

Preferably $R_{29}$ represents methyl or ethyl and h represents 0.

In preferred compounds of formula I, $R_1$, $R_2$ and $R_3$ independently represent hydrogen, halo (fluoro, chloro or bromo), trifluoromethyl, hydroxy($C_{1-4}$)alkyl (hydroxymethyl, hydroxyethyl, hydroxypropyl hydroxybutyl), $C_{1-4}$ alkyl (methyl, ethyl, propyl butyl), $C_{1-4}$ alkoxy (methoxy, ethoxy, propoxy, butoxy) or $C_{1-4}$alkylthio (methylthio, ethylthio, propylthio, butylthio). More preferably $R_1$, $R_2$ and $R_3$ independently represent hydrogen, fluoro, chloro, trifluoromethyl, hydroxymethyl, hydroxyethyl, methyl, methoxy or ethoxy. Most preferably, $R_1$ and $R_3$ represent hydrogen and $R_2$ represents hydrogen, halo, trifluoromethyl, $C_{1-6}$ alkyl, $C_{1-6}$ alkoxy or $C_{1-6}$ alkylthio, or $R_2$ and $R_3$ represent hydrogen and $R_1$ together with X and the phenyl group to which they are attached form a tetrahydronaphthyl group. Most preferably $R_1$ and $R_3$ represent hydrogen and $R_2$ represents hydrogen, chloro, trifluoromethyl, methyl, methoxy or methylthio.

In one group of compounds of formula I, X represents a bond and $alk^1$ is directly linked to the phenyl ring. In another group of compounds $alk^1$ is linked to the phenyl ring via a sulphur or oxygen atom, vinylene, carbonyl or —NHCO—. In a further group of compounds, $R_1$ and X together form a tetramethylene chain (so that with the phenyl group to which they are attached is formed a tetrahydronaphthyl group) and $alk^1$ replaces a hydrogen atom at the 1-, 2-, 3- or 4-position of the chain.

In further preferred compounds of formula I, $alk^1$ represents a $C_{1-4}$ alkylene chain (methylene, ethylene, trimethylene or tetramethylene) optionally substituted by one or two $C_{1-4}$ alkyl groups (methyl, ethyl, propyl or butyl), more preferably a $C_{1-3}$ alkylene chain. Most preferably $alk^1$ represents ethylene or trimethylene. In particularly preferred compounds of formula I, three optionally substituted atoms linked in a chain (preferably carbon atoms) connect the phenyl ring with group Y, for example, the following combinations of X, $alk^1$ and $(CO)_b$ are given:

(a) X represents a bond and $alk^1$ represents trimethylene, (b) X represents a sulphur or oxygen atom or carbonyl and $alk^1$ represents ethylene, (c) X represents vinylene or —NHCO— and $alk^1$ represents methylene.

In the above cases, b is 0. When b is 1, preferably X is a bond and $alk^1$ is ethylene.

In one group of compounds of formula I, b is 1 and therefore a carbonyl group links $alk^1$ with Y. In another group of compounds of formula I, b is 0 and therefore $alk^1$ is directly linked to Y.

In one group of preferred compounds of formula I, b is 0 and $alk^1$ represents $C_{1-4}$ alkylene. In a further preferred group, X is a bond, b is 0 and $alk^1$ represents $C_{1-4}$ alkylene. In a still further group of compounds X is a bond, b is 1 and $alk^1$ represents $C_{1-4}$ alkylene.

The ring Y may be linked to the chain $-alk^1-(CO)_b-$ through any position, eg through positions 1, 2, 3, 4 or 5 and, where the size of the ring permits, through position 6. Also the group Y may be linked to the chain $---(CR_8)_k-alk^2-$ through any position, other than through the atom which is linked to the $-alk^1-CO)_b-$ chain, eg through positions 1, 2, 3, 4 or 5 and, where the size of the ring permits, through position 6. In a preferred group of compounds of formula I, Y represents a pyrrolidinediyl group, a piperidinediyl group or a piperazinediyl group, optionally substituted as hereinbefore described. In a further preferred group of compounds of formula I, Y represents a group of formula II (variations (a), (b) and (c))

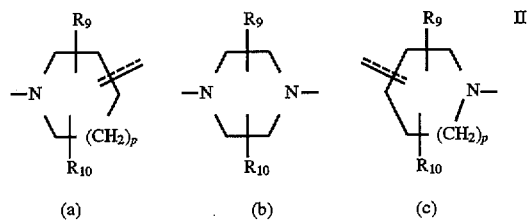

in which p is 0 or 1 and $R_9$ and $R_{10}$ independently represent hydrogen, $C_{1-6}$ alkyl, hydroxy($C_{1-6}$)alkyl or ($C_{1-6}$)alkoxy ($C_{1-6}$)alkyl. Preferably p is 1.

When $R_9$ and $R_{10}$ either together or separately are other than hydrogen, the substituent may replace any hydrogen attached to a carbon atom and may be located at any position in the ring Y, eg at positions 2, 3, 4, 5 or 6. Preferably $R_9$ and $R_{10}$ independently represent hydrogen or $C_{1-4}$ alkyl (methyl, ethyl, propyl or butyl), more preferably hydrogen or methyl. Most preferably $R_9$ and $R_0$ represent hydrogen.

Preferably Y is linked to the chain $-alk^1-(CO)_b-$ through a nitrogen atom and represents 1,2-piperidinediyl, 1,3-piperidinediyl, 1,4-piperidinediyl or 1,4-piperazinediyl or Y is linked to the chain $---(CR_8)_k-alk^2-$ through a nitrogen atom and represents 1,4-piperidinediyl. Each of the above preferred groups Y is optionally substituted by $C_{1-6}$ alkyl, hydroxy($C_{1-6}$)alkyl or ($C_{1-6}$)alkoxy($C_{1-6}$)alkyl.

In especially preferred compounds Y represents a group of formula III (variations (a), (b), (c), (d) and e))

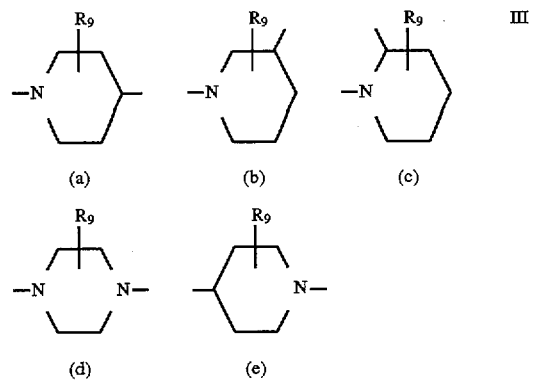

in which $R_9$, and preferred values thereof, are as defined above.

Most preferably Y is represented by groups IIIa or IIIb and $R_9$ represents hydrogen or methyl.

In one group of compounds of formula I, when k is 1 and $(CR_8)_k$ is linked to a carbon atom in the group Y, there is a double bond between Y and $CR_8$. In preferred compounds of formula I k is 0, thus the optional bond in $---/-13$ is absent and there is a single bond between Y and $alk^2$.

In preferred compounds of formula I, $R_8$ represents hydrogen, methyl or ethyl.

In preferred compounds of formula I, $alk^2$ represents a $C_{1-4}$ alkylene chain (methylene, ethylene, trimethylene, tetramethylene) optionally substituted by one or two $C_{1-4}$ alkyl groups (methyl, ethyl, propyl, butyl). More preferably $alk^2$ represents a $C_{1-3}$ alkylene chain, especially ethylene. In particularly preferred compounds of formula I, two optionally substituted carbon atoms are linked in a chain connecting the group Y with the group Z, for example k is 0 and $alk^2$ is ethylene.

In the most preferred compounds of formula I, $alk^1$ and $alk^2$ represent $C_{2-4}$ alkylene.

The ring system Z is linked to the chain $-alk^2-$ through a nitrogen atom. In a preferred group of compounds of formula I, Z represents an imidazolyl group, a triazolyl group (eg 1,2,3-triazolyl and 1,2,4-triazolyl), a tetrazolyl group, an imidazopyridyl group (eg, imidazo[1,2-a]-pyridyl and imidazo[3,4-a]pyridyl) or a benzimidazolyl group, each optionally substituted as hereinbefore described. In a further preferred group of compounds, Z represents an aromatic 5-membered heterocyclic ring containing 2-3 nitrogen atoms (especially 2 nitrogen atoms) optionally having a benzene ring or a pyridine ring fused thereto. The nitrogen atom of the optionally fused pyridine ring may be contained in the aromatic 5- membered ring or may be located in any of the non-bridgehead positions of the fused 6- membered ring.

More preferably Z may be represented by a group of formula IV

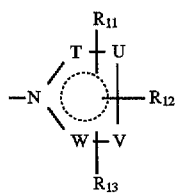

in which T, U, V and W independently represent N or CH to form an imidazolyl, triazolyl or tetrazolyl ring and $R_{11}$, $R_{12}$ and $R_{13}$ independently represent hydrogen, $C_{1-12}$ alkyl, halo, trifluoromethyl cyano; hydroxy; $C_{1-6}$ alkoxy, $C_{1-6}$alkoxy $(C_{1-6})$alkyl; $C_{2-6}$alkoxycarbonyl; carboxy; carboxy$(C_{1-6})$ alkyl; nitro, $C_{2-6}$alkoxycarbonyl$(C_{1-6})$alkyl; $C_{2-6}$alkanoyl; $C_{2-6}$alkanoyl$(C_{1-6}$alkyl$)$ —$NR_4R_5$; $R_6R_7N(C_{1-6})$alkyl; $CONR_{16}R_{17}$; $R_{18}R_{19}NCO(C_{1-6})$alkyl; $S(O)_mR_{20}$; a phenyl group optionally substituted by $C_{1-6}$ alkyl, $C_{1-6}$ alkoxy, trifluoromethyl or halo; a benzoyl group optionally substituted by $C_{1-6}$alkyl, $C_{1-6}$alkoxy, trifluoromethyl or halo; or a benzyl group optionally substituted by $C_{1-6}$ alkyl, $C_{1-6}$ alkoxy, trifluoromethyl or halo; or $R_{11}$ and $R_{12}$ together with the ring to which they are attached from a benzimidazolyl group or an imidazopyridyl group optionally substituted by one or more groups selected from $C_{1-12}$ alkyl, halo, trifluoromethyl, $C_{1-6}$ alkoxy, $C_{1-6}$alkoxy$(C_{1-6})$alkyl; $C_{2-6}$ alkoxycarbonyl; carboxy; carboxy$(C_{1-6})$alkyl; cyano, hydroxy; nitro; $C_{2-6}$alkoxycarbonyl$(C_{1-6})$alkyl; $C_{2-6}$alkanoyl; $C_{2-6}$alkanoyl$(C_{1-6})$-alkyl; —$NR_4R_5$, $R_6R_7N$ $(C_{1-6})$alkyl; $CONR_{16}R_{17}$; $R_{18}R_{19}NCO(C_{1-6})$alkyl; $S(O)_m$ $R_{20}$; a phenyl group optionally substituted by $C_{1-6}$ alkyl, $C_{1-6}$ alkoxy, trifluoromethyl or halo; a benzoyl group optionally substituted by $C_{1-6}$ alkyl, $C_{1-6}$alkoxy, trifluoromethyl or halo or a benzyl group optionally substituted by $C_{1-6}$ alkyl, $C_{1-6}$ alkoxy, trifluoromethyl or halo. When $R_{11}$, $R_{12}$ and $R_{13}$ represent other than hydrogen, that substituent may replace any hydrogen attached to a carbon atom in the aromatic heterocyclic ring system. Preferably the optional phenyl, benzoyl and benzyl groups are unsubstituted or are substituted with one or two substituents as herein defined (preferably when said groups include at least one substituent, at least one substituent is located at the 3 and/or 4 position).

Preferably $R_4$, $R_5$, $R_6$, $R_7$, $R_{16}$, $R_{17}$, $R_{18}$ and $R_{19}$ independently represent hydrogen, methyl or ethyl. Preferably $R_{20}$ represents methyl or ethyl and m represents 2.

Especially preferred are compounds in which the ring system represented by formula IV, in which the number refers to the ring position attached to the chain -alk$^2$-, is imidazol-1-yl, 1,2,4-triazol-1-yl, 1,2,3-triazol-1-yl, 1,2,3-triazol-2-yl, 1,2,4-triazol-4-yl, tetrazol-2-yl, benzimidazol-1-yl, each optionally substituted as hereinabove described. Most preferably Z represents a group of formula V (variations (a) to (h))

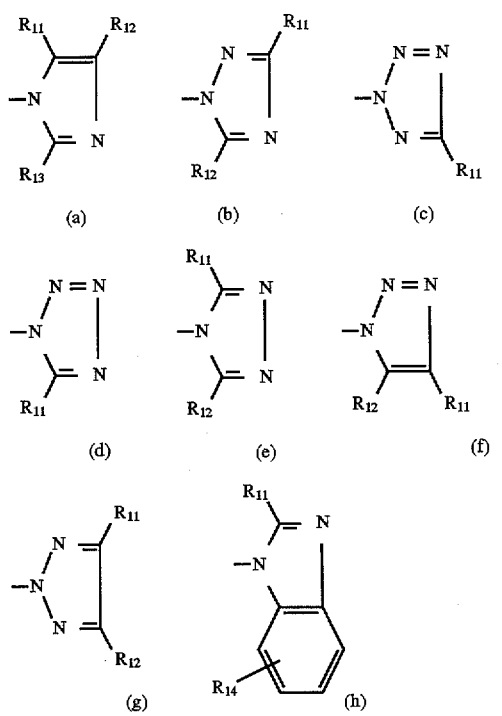

in which $R_{11}$, $R_{12}$ and $R_{13}$ are described hereinabove and $R_{14}$ represents hydrogen, $C_{1-6}$ alkyl, halo, trifluoromethyl, $C_{1-6}$ alkoxy, $C_{1-6}$ alkoxy$(C_{1-6})$alkyl; $C_{2-6}$ alkoxycarbonyl; nitro, —$NR_4R_5$, $R_6R_7N(C_{1-6})$alkyl; $S(O)_mR_{20}$; a phenyl group optionally substituted by $C_{1-6}$ alkyl, $C_{1-6}$ alkoxy or halo; a benzoyl group optionally substituted by $C_{1-6}$ alkyl, $C_{1-6}$ alkoxy or halo; or a benzyl group optionally substituted by $C_{1-6}$ alkyl, $C_{1-6}$ alkoxy or halo.

In valuable compounds of formula I Z is selected from imidazol-1-yl, 1,2,4-triazol-1-yl, 1,2,3-triazol-1-yl, 1,2,3-triazol-2-yl, tetrazol-2-yl or benzimidazol-1-yl, each of which groups is optionally substituted by one to three groups selected from halo, trifluoromethyl, $C_{1-12}$alkyl, phenyl or benzoyl, said phenyl or benzoyl groups being optionally substituted by halo. Of these, the most preferred is imidazol-1-yl (Group Va) optionally substituted by one, two or three groups selected from halo, $C_{1-12}$alkyl, phenyl or benzoyl, said phenyl or benzoyl groups being optionally substituted by halo.

When $R_{14}$ is other than hydrogen, that substituent may replace any hydrogen attached to a carbon atom in the benzene ring.

Preferably $R_{11}$, $R_{12}$, $R_{13}$ and $R_{14}$ independently represent hydrogen, halo (fluoro, chloro or bromo), $C_{1-12}$ alkyl (eg methyl, ethyl, propyl, butyl up to and including undecyl and dodecyl); $C_{1-4}$ alkoxy (methoxy, ethoxy, propoxy or butoxy); phenyl; or benzoyl optionally substituted by halo (eg chloro). More preferably $R_{12}$ and $R_{13}$ represent hydrogen and $R_{11}$ and $R_{14}$ represent hydrogen, chloro, methyl, ethyl, propyl, undecyl, phenyl, 2-chlorobenzoyl. Most preferably $R_{11}$ represents hydrogen. Most preferably $R_{14}$ represents hydrogen.

Preferred compounds of formula I are those represented by formula VI

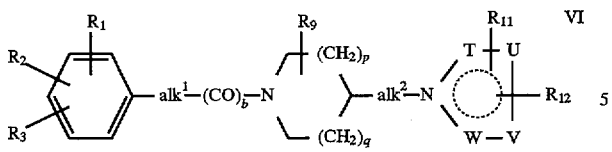

in which p is 0 or 1, q is 0 or 1 and p+q is 1 or 2 and $alk^1$, $alk^2$, $R_1$, $R_2$, $R_3$, $R_9$, $R_{11}$, $R_{12}$, T, U, V, W, b and preferred values thereof, are as hereinabove described.

More preferred compounds of formula are represented by compounds of formula VII

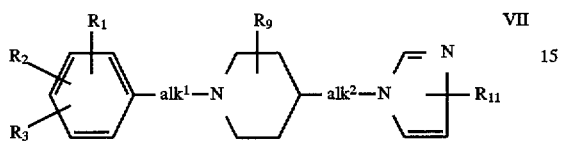

in which $alk^1$, $alk^2$, $R_1$, $R_2$, $R_3$, $R_9$ and $R_{11}$, and preferred substituents thereof, are as hereinabove described.

A valuable group of compounds of formula I are those in which $R_1$, $R_2$ and $R_3$ independently represent hydrogen; halo; cyano; hydroxy($C_{1-6}$)alkyl; $C_{1-6}$ alkyl (optionally halogenated); $C_{1-6}$ alkoxy (optionally halogenated); $C_{2-6}$ alkanoyl; $C_{2-6}$ alkoxycarbonyl; $C_{2-6}$alkoxycarbonyl($C_{1-6}$)alkyl; carboxy; nitro; imidazolyl; carboxy($C_{1-6}$)alkyl; $C_{2-6}$alkanoyl($C_{1-6}$)alkyl; $C_{1-6}$alkoxy($C_{1-6}$)alkyl; $NR_{21}R_{22}$; $R_{23}R_{24}N(C_{1-6})$alkyl; $CONR_{25}R_{26}$; $R_{27}R_{28}NCO(C_{1-6})$alkyl; $S(O)_hR_{29}$; a phenyl group, a phenoxy group, or a benzyloxy group, or $R_1$ and $R_2$ together with the phenyl group to which they are attached form a naphthyl group, or $R_1$ together with X and the phenyl group to which they are attached form a tetrahydronaphthyl group; each of said phenyl, phenoxy, benzyloxy or naphthyl groups being optionally substituted by halo, $C_{1-6}$ alkyl or $C_{1-6}$ alkoxy; $R_{21}$ and $R_{22}$ independently represent hydrogen or $C_{1-6}$ alkyl or $R_{21}$ and $R_{22}$ together with the nitrogen to which they are attached form a 1-pyrrolidinyl group, a morpholino group or a piperidino group; $R_{23}$ and $R_{24}$ independently represent hydrogen or $C_{1-6}$ alkyl or $R_{23}$ and $R_{24}$ together with the nitrogen to which they are attached form a 1-pyrrolidinyl group, a morpholino group or a piperidino group; $R_{25}$ and $R_{26}$ independently represent hydrogen or $C_{1-6}$ alkyl; $R_{27}$ and $R_{28}$ independently represent hydrogen or $C_{1-6}$ alkyl; $R_{29}$ represents $C_{1-6}$ alkyl; h represents 0 or 1;

X represents a bond;

$alk^1$ represents a $C_{1-6}$ alkylene chain optionally substituted by one or more $C_{1-4}$ alkyl groups;

b represents 0;

Y represents a saturated 5 or 6 membered heterocyclic ring containing one or two nitrogen atoms, the ring optionally substituted by one or two groups selected from $C_{1-6}$ alkyl and hydroxy($C_{1-6}$)alkyl;

$R_8$ represents hydrogen or $C_{1-4}$ alkyl; k represents 0 or 1 provided that when k is 1, $CR_8$ is linked to a carbon atom in the group Y;

the dotted line in _ _ _ represents a bond when $-(CR_8)_k$ is linked to a carbon atom in the group Y and k represents 1, the dotted line does not represent a bond when k is 0;

$alk^2$ represents a $C_{1-6}$ alkylene chain optionally substituted by one or more $C_{1-4}$ alkyl groups;

Z represents an aromatic heterocyclic ring system comprising a 5 membered ring selected from imidazolyl, triazolyl and tetrazolyl, each ring being connected to $alk^2$ via a nitrogen atom and each ring optionally having a benzene ring or a pyridine ring fused thereto, the ring system being optionally substituted by one, two or three groups selected from halo; cyano; hydroxy; nitro; $C_{1-6}$ alkyl; $C_{1-6}$ alkoxy; carboxy, carboxy($C_{1-6}$)alkyl; $C_{1-6}$alkoxy($C_{1-6}$)alkyl; $C_{2-6}$alkoxycarbonyl; $C_{2-6}$alkoxycarbonyl($C_{1-6}$)alkyl; $C_{2-6}$alkanoyl; $C_{2-6}$alkanoyl($C_{1-6}$)alkyl; $NR_4R_5$; $R_6R_7N(C_{1-6})$alkyl; $CONR_{16}R_{17}$; $R_{18}R_{19}NCO(C_{1-6})$alkyl; $S(O)_mR_{20}$; a phenyl group optionally substituted by $C_{1-6}$ alkyl, $C_{1-6}$ alkoxy or halo; and a benzyl group optionally substituted by $C_{1-6}$ alkyl, $C_{1-6}$ alkoxy or halo; $R_4$ and $R_5$ independently represent hydrogen or $C_{1-6}$ alkyl or $R_4$ and $R_5$ together with the nitrogen to which they are attached form a 1-pyrrolidinyl group, a morpholino group or a piperidino group; $R_6$ and $R_7$ independently represent hydrogen or $C_{1-6}$ alkyl or $R_6$ and $R_7$ together with the nitrogen to which they are attached form a 1-pyrrolidinyl group, a morpholino group or a piperidino group; $R_{16}$ and $R_{17}$ independently represent hydrogen or $C_{1-6}$ alkyl; $R_{18}$ and $R_{19}$ independently represent hydrogen or $C_{1-6}$ alkyl; $R_{20}$ represents $C_{1-6}$ alkyl; and m represents 0, 1 or 2.

Particularly preferred compounds of formula I are:

4-[2-(Imidazol-1-yl)ethyl]-1-(3-phenylpropionyl)piperidine
2-[2-(Imidazol-1-yl)ethyl]-1-(3-phenylpropionyl)piperidine
3-Imidazol-1-ylmethyl-1-(3-phenylpropionyl)piperidine
4-[3-(Imidazol-1-yl)propyl]-1-(3-phenylpropionyl)piperidine
1-[3-(4-Chlorophenyl)propionyl]-4-[2-(2-methylimidazol-1-yl)ethyl]piperidine
4-[2-(2-Isopropylimidazol-1-yl)ethyl]-1-(3-phenylpropionyl)piperidine
1-(3-Phenylpropionyl)-4-[2-(2-undecylimidazol-1-yl)ethyl]piperidine
2-Methyl-1-{2-[1-(3-phenylpropionyl)piperidin-4-yl]ethyl}benzimidazole
4-(2-Ethylimidazol-1-ylmethyl)-1-(3-phenylpropionyl)piperidine
4-[2-(2-Methylimidazol-1-yl)ethyl]-1-(3-phenylpropionyl)piperidine
4-[2-(2-Methylimidazol-1-yl)ethyl]-1-(4-phenylbutyroyl)piperidine
4-[2-(Imidazol-1-yl)ethyl]-1-(4-phenylbutyroyl)piperidine
4-[2-(Imidazol-1-yl)ethyl]-1-(2-phenylthioethyl)piperidine
4-[2-(Imidazol-1-yl)ethyl]-1-(2-phenoxyethyl)piperidine
4-[2-(Imidazol-1-yl)ethyl]-1-(4-oxo-4-phenylbutyl)piperidine
4-[2-(Imidazol-1-yl)ethyl]-1-(3-oxo-3-phenylpropyl)piperidine
1-Cinnamyl-4-[2-(imidazol-1-yl)ethyl]piperidine
4-[2-(Imidazol-1-yl)ethyl]piperidino-4'-trifluoromethylacetanilide
4-{2-[2-(2-Chlorobenzoyl)imidazol-1-yl]ethyl}-1-(3-phenylpropyl)piperidine
1-[1-(4-chlorophenyl)ethyl]-4-[2-(imidazol-1-yl)ethyl]piperidine
4-[2-(2-methylimidazol-1-yl)ethyl]-1-[3-(4-methylphenyl)propionyl]piperidine
1-[2-(Imidazol-1-yl)ethyl]-4-(3-phenylpropyl)piperazine
1-[2-(Imidazol-1-yl)ethyl]-4-(3-phenylpropyl)piperidine
1-[2-(1H-1,2,4-triazol-1-yl)ethyl]-4-(3-phenylpropyl)piperidine
4-[2-(Imidazol-1-yl)ethyl]-1-(3-phenylpropyl)piperidine
3-[2-(Imidazol-1-yl)ethyl]-1-(3-phenylpropyl)piperidine
2-[2-(Imidazol-1-yl)ethyl]-1-(3-phenylpropyl)piperidine
3-Imidazol-1-ylmethyl-1-(3-phenylpropyl)piperidine
4-Imidazol-1-ylmethyl-1-(3-phenylpropyl)piperidine
4-[2-(Imidazol-1-yl)ethyl]-3-methyl-1-(3-phenylpropyl)piperidine 4-[3-(Imidazol-1-yl)propyl]-1-(3-phenylpropyl)piperidine
1-[3-(4-Chlorophenyl)propyl]-4-[2-(2-methylimidazol-1-yl) ethyl]piperidine
4-[2-(2-Isopropylimidazol-1-yl)ethyl]-1-(3-phenylpropyl) piperidine
4-[2-(2-Ethylimidazol-1-yl)ethyl]-1-(3-phenylpropyl) piperidine
4-[2-(4,5-Diphenylimidazol-1-yl)ethyl]-1-(3-phenylpropyl) piperidine
4-[2-(2-Phenylimidazol-1-yl)ethyl]-1-(3-phenylpropyl) piperidine
1-(3-Phenylpropyl)-4-[2-(2-propylimidazol-1-yl)ethyl] piperidine
1-(3-Phenylpropyl)-4-[2-(1H-1,2,4-triazol-1-yl)ethyl]piperidine
2-Methyl-1-{2-[1-(3-phenylpropyl)piperidin-4-yl]ethyl}benzimidazole
4-[2-(Imidazol-1-yl)-1-methylethyl]-1-(3-phenylpropyl)piperidine
1-{2-[1-(3-phenylpropyl)piperidin-4-yl]ethyl}benzimidazole
4-[2-(4,5-Dichloro-2-methylimidazol-1-yl)ethyl]-1-(3-phenylpropyl)piperidine
4-[2-(4,5-Dimethylimidazol-1-yl)ethyl]-1-(3-phenylpropyl) piperidine
4-[2-(2-Methylimidazol-1-yl)ethyl]-1-(3-phenylpropyl) piperidine
4-[2-(4-Methylimidazol-1-yl)ethyl]-1-(3-phenylpropyl) piperidine
4-[2-(5-Methylimidazol-1-yl)ethyl]-1-(3-phenylpropyl) piperidine
1-(3-Phenylpropyl)-4-[2-(1H-1,2,3-triazol-1-yl)ethyl]piperidine
1-(3-Phenylpropyl)-4-[2-(2H-1,2,3-triazol-2-yl)ethyl]piperidine
1-(3-Phenylpropyl)-4-[2-(2H-tetrazol-2-yl)ethyl]piperidine
4-[2-(Imidazol-1-yl)ethyl]-1-[3-(4-methylphenyl)propyl] piperidine
1-[3-(4-Chlorophenyl)propyl]-4-[2-(imidazol-1-yl)ethyl] piperidine
4-[2-(Imidazol-1-yl)ethyl]-1-[3-(4-methoxyphenyl)propyl] piperidine
4-[2-(Imidazol-1-yl)ethyl]-1-(1,2,3,4-tetrahydronaphth-2-ylmethyl)piperidine
4-[2-(Imidazol-1-yl)ethyl]-1-(3-phenylbutyl)piperidine
4-[2-(Imidazol-1-yl)ethyl]-1-[3-(4-methylthiophenyl) propyl]piperidine
4-[2-(Imidazol-1-yl)ethyl]-1-phenethylpiperidine
4-[2-(Imidazol-1-yl)ethyl]-1-(4-phenylbutyl)piperidine
including salts, hydrates or solvates thereof.

Further preferred compounds are identified in Tables A and B hereinafter provided.

Compounds of formula I may contain one or more chiral centres and exist in different optically active forms. When compounds of formula I contain one chiral centre the compounds exist in two enantiomeric forms and the present invention includes both enantiomers and mixtures of enantiomers. The enantiomers may be resolved by methods known to those skilled in the art, for example by formation of diastereoisomeric salts which may be separated, for example, by crystallisation; formation of diastereoisomeric derivatives or complexes which may be separated, for example, by crystallisation, gas-liquid or liquid chromatography; selective derivatisation of one enantiomer by reaction with an enantiomer-specific reagent, for example enzymatic oxidation or reduction; or gas-liquid or liquid chromatography in a chiral environment, for example on a chiral support, for example silica with a bound chiral ligand or in the presence of a chiral solvent. It will be appreciated that where the active moiety is transformed by the separation procedures described above, a further step may be required to convert the product to the active moiety. Alternatively, specific enantiomers may be synthesised by asymmetric synthesis using optically active reagents, substrates, catalysts or solvents, by enzymatic processes, or by converting one enantiomer into the other by asymmetric transformation.

When compounds of formula I contain more than one chiral centre, the compounds may exist in diastereoisomeric forms. The present invention includes each diastereoisomer and mixtures of the diastereoisomers. The diastereoisomers may be separated by methods known to those skilled in the art, for example by crystallisation or liquid chromatography.

In particular, the following compounds exist as racemates, therefore the present invention includes both racemic and R— and S— enantiomeric forms of:

3-[2-(Imidazol-1-yl)ethyl]-1-(3-phenylpropyl)piperidine
2-[2-(Imidazol-1-yl)ethyl]-1-(3-phenylpropyl)piperidine
3-Imidazol-1-ylmethyl-1-(3-phenylpropyl)piperidine
4-[2-(Imidazol-1-yl)ethyl]-3-methyl-1-(3-phenylpropyl) piperidine
4-[2-(Imidazol-1-yl)-1-methylethyl]-1-(3-phenylpropyl) piperidine
4-[2-(Imidazol-1-yl)ethyl]-1-(2H-1,2,3,4-tetrahydronaphth-2-ylmethyl)piperidine
4-[2-(Imidazol-1-yl)ethyl]-1-(3-phenylbutyl)piperidine
2-[2-(Imidazol-1-yl)ethyl]-1-(3-phenylpropionyl)piperidine
3-Imidazol-1-ylmethyl-1-(3-phenylpropionyl)piperidine
1-[1-(4-Chlorophenyl)ethyl]-4-[2-(imidazol-1-yl)ethyl] piperidine Certain compounds of formula I may exist in different tautomeric forms or as different geometric isomers.

Compounds of formula I are bases and may form salts with inorganic or organic acids, for example the compounds of formula I may form acid addition salts with inorganic or organic acids, e.g. hydrochloric acid, hydrobromic acid, fumaric acid, tartaric acid, citric acid, sulphuric acid, hydroiodic acid, phosphoric acid, maleic acid, acetic acid, succinic acid, benzoic acid, pamoic acid, palmitic acid, dodecanic acid and acidic amino acids such as glutamic acid. Some compounds of formula I may form base addition salts, for example, with alkalis for example sodium hydroxide, or with aminoacids for example, lysine or arginine. It will be appreciated that such salts, provided they are pharmaceutically acceptable, may be used in therapy in place of the corresponding compounds of formula I. Such salts may be prepared for example by reacting the compound of formula I with a suitable acid or base in a conventional manner.

Certain compounds of formula I may exist in more than one crystal form and the present invention includes each crystal form and mixtures thereof.

Certain compounds of formula I may also exist in the form of solvates, for example hydrates, and the present invention includes each solvate and mixtures thereof. The degree of hydration may be non-stoichiometric and is preferably in the range 0 to 3, for example a hemihydrate, a monohydrate or a dihydrate.

The present invention also includes pharmaceutical compositions containing a therapeutically effective amount of a compound of formula I together with a pharmaceutically acceptable diluent or carrier.

As used hereinafter, the term "active compound" denotes a compound of formula I. In therapeutic use, the active compound may be administered orally, rectally, parenterally or topically, preferably orally or topically. The compounds may provide a local and/or systemic therapeutic effect or they may be administered in a prophylactic manner. Thus the therapeutic compositions of the present invention take the form of any of the known pharmaceutical compositions for oral, rectal, parenteral or topical administration. Pharmaceutically acceptable carriers suitable for use in such compositions are well known in the art of pharmacy. The compositions of the invention may contain 0.1–90% by weight of active compound. The compositions of the invention are generally prepared in unit dosage form. The excipients used in the preparation of these compositions are the excipients known in the pharmacist's art.

Compositions for oral administration are preferred compositions of the invention and these are known pharmaceutical forms for such administration, for example tablets, capsules, syrups and aqueous or oily suspensions. Tablets may be prepared by mixing the active compound with an inert diluent such as lactose or calcium phosphate in the presence of disintegrating agents, for example maize starch, and lubricating agents, for example magnesium stearate, and tableting the mixture by known methods. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by conventional means and, if desired, provided with enteric coatings in a known manner. The tablets and capsules may conveniently each contain 0.1 to 500 mg (for example 10 mg, 50 mg, 100 mg or 200 mg) of the active compound. Other compositions for oral administration include, for example, aqueous suspensions containing the active compound in an aqueous medium in the presence of a nontoxic suspending agent such as sodium carboxymethylcellulose, and oily suspensions containing a compound of the present invention in a suitable vegetable oil, for example arachis oil.

Compositions for topical administration are also preferred compositions of the invention. The pharmaceutically active compound may be dispersed in a pharmaceutically acceptable cream, ointment or gel. A suitable cream may be prepared by incorporating the active compound in a topical vehicle such as petrolatum and/or light liquid paraffin, dispersed in an aqueous medium using surfactants. An ointment may be prepared by mixing the active compound with a topical vehicle such as a mineral oil, petrolatum and/or a wax e.g. paraffin wax or beeswax. A gel may be prepared by mixing the active compound with a topical vehicle comprising a gelling agent e.g. basified Carbomer BP, in the presence of water. Topically administrable compositions may also comprise a matrix in which the pharmaceutically active compounds of the present invention are dispersed so that the compounds are held in contact with the skin in order to administer the compounds transdermally. A suitable transdermal composition may be prepared by mixing the pharmaceutically active compound with a topical vehicle, such as described above, together with a potential transdermal accelerant such as dimethyl sulphoxide or propylene glycol.

Compositions of the invention suitable for rectal administration are known pharmaceutical forms for such administration, for example suppositories with semisynthetic glycerides or polyethylene glycol bases.

Compositions of the invention suitable for parenteral administration are known pharmaceutical forms for such administration, for example sterile suspensions in aqueous and oily media or sterile solutions in a suitable solvent.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The compounds of formula I are indicated for use as immunomodulatory agents, and are generally immunosuppressants. The compounds according to the invention are useful in the treatment of diseases resulting from an aberrant immune reaction. Thus the pharmaceutical compositions containing a therapeutically effective amount of a compound of formula I may be used to treat diseases with an immunological association. The compounds are useful to treat immunologically-induced diseases including allergic and inflammatory conditions, particularly those mediated by the release of cytokines such as tumour necrosis factor. Compounds of formula I and pharmaceutically acceptable salts thereof are also indicated for use in the treatment of inflammatory conditions.

The therapeutic activity of compounds falling within formula I has been demonstrated by means of in vitro and in vivo tests. Such tests include, for example, the in vitro mixed lymphocyte reaction test and the arachidonic acid release test and the in vivo mouse tumour necrosis factor (TNF) test and paw oedema test. Thus, compounds of formula I are useful as immunomodulatory agents, anti-inflammatory agents and anti-allergic agents.

Diseases which may be treated by compounds according to the present invention include immunologically based diseases such as transplant rejection, eg kidney rejection; and graft-versus-host disease; joint inflammation; autoimmune diseases, such as rheumatoid arthritis, thyroiditis, type 1 diabetes, multiple sclerosis, sarcoidosis and systemic lupus erythematosus; cutaneous disorders, such as contact sensitivity, eczema and psoriasis; respiratory disorders for example: asthma and rhinitis; gastrointestinal disorders for example: gastritis, Crohn's disease, ulcerative colitis and other inflammatory diseases of the bowel; diseases of the oral cavity for example: periodontitis and gingivitis; HIV infection (AIDS); sepmic shock; malaria. Diseases also treated by anti-inflammatory agents additionally include osteoarthritis, muscle trauma, gout, ankylosing spondylitis, tendonitis and bursitis; Alzheimer's Disease; cutaneous disorders for example: urticaria, allergic skin diseases, burns, occular inflammation and iritis. Compounds of formula I and salts thereof may also be useful as analgesics and/or anti-pyretic agents.

Whilst the precise amount of active compound administered will depend on a number of factors, for example the age of the patient, the severity of the condition and the past medical history and always lies within the sound discretion of the administering physician, a suitable dose for oral administration to mammals, including humans, is generally within the range 0.1 to 2000 mg per day, preferably 1–500 mg per day. Doses may fall within the range 0.01–40 mg/kg/day, more usually 0.2–25 mg/kg/day given in single or divided doses. For parenteral administration, a suitable dose is generally within the range 0.001–4.0 mg/kg/day, more usually 0.005–1 mg/kg/day given in single or divided doses or by continuous infusion. A suitable preparation for topical administration generally contains the active ingredient within the range 0.01–20% by weight, more usually 0.05–5% by weight. Oral administration is preferred.

Accordingly, in another aspect, the present invention also includes a method of treating diseases with an immunological association in a mammal in need of such treatment, comprising the administration of a therapeutically effective amount of a compound of formula I to said mammal.

The present invention also includes a method of treating inflammatory and/or allergic conditions in a mammal in need of such treatment comprising the administration of a therapeutically effective amount of a compound of formula I to said mammal.

Processes for the preparation of compounds of formula I will now be described. These processes form a further aspect of the present invention.

A compound of formula I in which Y is represented by the group IIa or IIb and b represents 1 may be prepared by the reaction between a compound of formula VIII

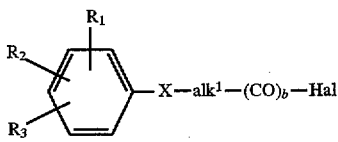

in which Hal represents halo, b represents 1, and $R_1$, $R_2$, $R_3$, X and $alk^1$ are as hereinabove defined, with a compound of formula IX

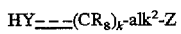

HY---$(CR_8)_k$-$alk^2$-Z     IX in which Y is represented by a group of formula IIa or IIb and Z, $R_8$, $alk^2$ and k are as hereinabove defined, for example by reacting at a temperature in the range 0°–200° C. in the presence of a base, eg triethylamine, optionally in the presence of an inert organic liquid, eg dichloromethane; preferably at a temperature in the range from 0° C. up to the boiling point of the inert organic liquid, eg 0°–50° C.

A compound of formula I in which Y is represented by the group IIa or IIb and b represents 0 may be prepared by the reaction between a compound of formula VIII in which b represents 0 with a compound of formula IX, for example by reacting in the presence of a base, eg sodium bicarbonate, in an inert organic liquid, eg industrial methylated spirits at a temperature in the range from 0° C. up to the boiling point of the inert organic liquid, eg 0°–200° C., preferably by heating at a temperature in the range 20°–150° C. It will be appreciated by those skilled in the art that this reaction may give rise to quaternary salt by-products, the compound of formula I may be separated by known techniques, eg distillation.

A compound of formula I in which Y is represented by the group IIa or IIb, X is other than carbonyl or —NHCO— and b and k represent 0 may be prepared by reducing a compound of formula X

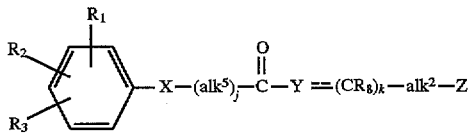

in which j is 1, X is other than carbonyl or —NHCO—, $alk^5$ represents $C_{1-5}$ alkylene optionally substituted by one or more $C_{1-4}$ alkyl groups, Y represents a group of formula IIa or IIb, and $R_1$, $R_2$, $R_3$, $R_8$, Z, $alk^2$ and k are as hereinabove defined, for example by reduction with borane in an inert organic liquid for example tetrahydrofuran, at a temperature in the range from 0° C. up to the boiling point of the inert organic liquid, eg 0°–200° C., preferably by heating at a temperature in the range 20°–150° C.

A compound of formula I in which Y is represented by the group IIa or IIb, X is other than carbonyl —NHCO—, a sulphur or oxygen atom and b and k represent 0 may be prepared by reducing a compound of formula X in which j is 0, Y represents a group of formula IIa or IIb, X is other than carbonyl, —NHCO— a sulphur or oxygen atom and $R_1$, $R_2$, $R_3$, $R_8$, Z, $alk^2$ and k are as hereinabove defined, for example by reduction with borane in an inert organic liquid for example tetrahydrofuran, at a temperature in the range from 0° C. up to the boiling point of the inert organic liquid, eg 0°–200° C., preferably by heating at a temperature in the range 20°–150° C.

A compound of formula I in which Y is represented by a group of formula IIa, and k represents 1 may be prepared by reacting a compound of formula XI

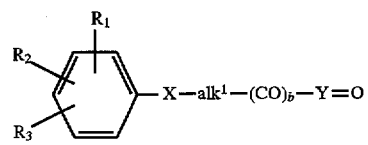

in which Y represents a group of formula IIa, and $R_1$, $R_2$, $R_3$, X, $alk^1$ and b are as hereinabove defined, with a Wittig reagent such as a compound of formula XIa

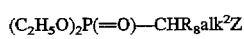

$(C_2H_5O)_2P(=O)$—$CHR_8alk^2Z$     XIa in which $R_8$, $alk^2$ and Z are as hereinbefore defined, (which has been treated with a base, eg sodium hydride, in an inert organic liquid, eg tetrahydrofuran) and the mixture combined in an inert organic liquid, eg tetrahydrofuran at a temperature in the range from 0° C. up to the boiling point of the inert organic liquid, eg 0°–200° C., preferably by heating at a temperature in the range 20°–150° C.

A compound of formula I in which Y is represented by a group of formula IIa and b and k represent 0 may be prepared by hydrogenating a compound of formula XII

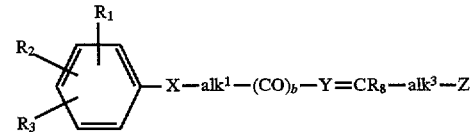

in which Y represents a group of formula IIa, $alk^3$ represents $C_{1-5}$ alkylene optionally substituted by one or more $C_{1-4}$ alkyl groups, b represents 0 and $R_1$, $R_2$, $R_3$, $R_8$, X, Z and $alk^1$ are as hereinabove defined, for example by reaction with hydrogen in the presence of a catalyst such as palladium on charcoal and in the presence of an inert organic liquid such as ethanol at a pressure in the range 1–10 atmospheres.

A compound of formula I in which Y is represented by a group of formula IIb or IIc and k is 0 may be prepared by reacting a compound of formula XIII

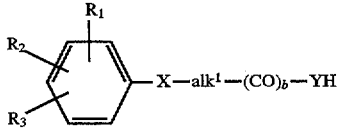

in which Y is represented by a group of formula IIb or IIc and $R_1$, $R_2$, $R_3$, X, $alk^1$ and b are as hereinabove defined, with a compound of formula XIV

Hal-$alk^2$-Z     XIV in which Hal represents halo, and $alk^2$ and Z are as hereinabove defined, for example in the presence of a base, for example triethylamine, in an inert organic liquid, eg toluene, at a temperature in the range from 0° C. up to the boiling point of the inert organic liquid, eg 0°–200° C., preferably by heating at a temperature in the range 20°–150° C. It will be appreciated by those skilled in the art that this reaction may give rise to quaternary salt by-products, the compound of formula I may be separated by known techniques, eg distillation.

A compound of formula I may be prepared by reacting a compound of formula XV

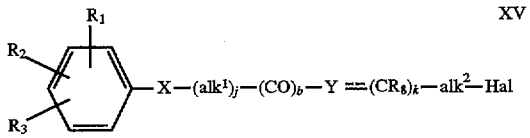

XV in which Hal represents halo, j represents 1 and $R_1$, $R_2$, $R_3$, $R_8$, X, Y, $alk^1$, $alk^2$, b and k are as hereinabove defined, with a compound of formula XVI

ZH           XVI in which Z is as hereinbefore defined, for example in an inert organic liquid, eg tetrahydrofuran, at a temperature in the range 0°–150° C. in the presence of a base, for example sodium hydride; preferably by heating at a temperature in the range 20°–150° C. It will be appreciated by those skilled in the art that this reaction may give rise to quaternary salt by-products, the compound of formula I may be separated by known techniques, eg distillation.

A compound of formula I in which Y is represented by the group IIa or IIb, X is other than carbonyl or —NHCO— and b and k represent 0 may be prepared by reducing a compound of formula XVII

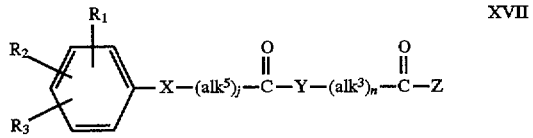

XVII in which Y represents a group IIa or IIb, X represents other than carbonyl or —NHCO—, $alk^3$ represents $C_{1-5}$ alkylene optionally substituted by one or more $C_{1-4}$ alkyl groups, $alk^5$ represents $C_{1-5}$ alkylene optionally substituted by one or more $C_{1-4}$ alkyl groups, j and n are 1 and $R_1$, $R_2$, $R_3$, Z are as hereinabove defined, for example by reaction with borane in an inert organic liquid at a temperature in the range from 0° C. up to the boiling point of the inert organic liquid, eg 0°–200° C., preferably by heating at a temperature in the range 20°–150° C., such as by heating in tetrahydrofuran under reflux.

A compound of formula I in which Y is represented by the group IIa or IIb, X is other than carbonyl, —NHCO—, a sulphur or oxygen atom and b and k represent 0 may be prepared by reducing a compound of formula XVII in which Y represents a group IIa or IIb, X represents other than carbonyl, —NHCO—, a sulphur or oxygen atom, j and n are 0 and $R_1$, $R_2$, $R_3$, Z, $alk^3$ and $alk^5$ are as hereinabove defined, for example by reaction with borane in a inert organic liquid at a temperature in the range from 0° C. up to the boiling point of the inert organic liquid, eg 0°–200° C., preferably by heating at a temperature in the range 20°–150° C., such as by heating in tetrahydrofuran under reflux.

A compound of formula I in which X represents a bond and Y is represented by a group of formula IIa or IIb and b and k represent 0 may be prepared by reducing a compound of formula XVIII

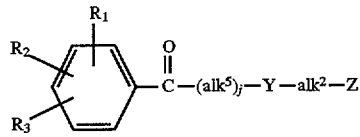

XVIII in which Y represents a group of formula IIa or IIb, $alk^5$ represents $C_{1-5}$ alkylene optionally substituted by one or more $C_{1-4}$ alkyl groups, and $R_1$, $R_2$, $R_3$, Z, $alk^2$, and j are as hereinabove defined, for example by reaction with a mixture of lithium aluminium hydride and aluminium chloride in an inert organic liquid such as diethyl ether at a temperature in the range from 0° C. up to the boiling point of the inert organic liquid, eg 0°–200° C., preferably by heating at a temperature in the range 20°–150° C.

A compound of formula I in which X represents a bond and Y is represented by a group of formula IIa or IIb and b and k represent 0 may be prepared by reducing a compound of formula XVIIIa

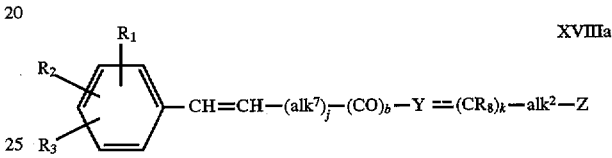

XVIIIa in which y represents a group of formula IIa or IIb, $alk^7$ represents $C_{1-4}$ alkylene optionally substituted by one or more $C_{1-4}$ alkyl groups when b is 0 or $alk^7$ represents $C_{1-3}$ alkylene optionally substituted by one or more $C_{1-4}$ alkyl groups when b is 1, j is 0 or 1, b is 0 or 1 and $R_1$, $R_2$, $R_3$, $R_8$, Z, $alk^2$, and k are as hereinabove defined, for example by reaction with borane in an inert organic liquid such as tetrahydrofuran at a temperature in the range from 0° C. up to the boiling point of the inert organic liquid, eg 0°–200° C., preferably by heating at a temperature in the range 20°–150° C., with the optional step of reaction with hydrogen in the presence of a catalyst such as palladium on charcoal and in the presence of an inert organic liquid such as ethanol at a pressure in the range 1–10 atmospheres.

Compounds of formulae VI and VII may be prepared in the same way as described above for compounds of formula I in which Y is represented by a group of formula IIa.

A compound of formula VIII may be prepared by halogenating a compound of formula XIX

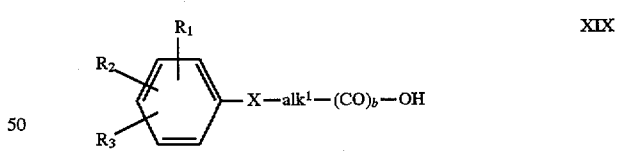

XIX in which X is other than —NHCO— and $R_1$, $R_2$, $R_3$, $alk^1$ and b are as hereinabove defined, for example by reaction with thionylchloride or oxalyl chloride, at a temperature in the range 0°–150° C. optionally in the presence of an inert organic liquid such as toluene or methylene chloride.

A compound of formula IX in which Y represents IIa or IIb and k is 0 may be prepared by hydrolysis of a compound of formula X, for example by reaction with dilute hydrochloric acid at a temperature in the range 0°–200° C., preferably by heating at a temperature in the range 20°–150° C. A compound of formula IX in which k is 1 may be prepared in a similar manner from a compound of formula XII in which b represents 1 and $alk^3$ represents $alk^2$.

A compound of formula IX in which Y represents IIa or IIb and k is 0 may also be prepared by reacting a compound of formula XX R'Y-alk²-Hal                                  XX in which R' represents a protecting group (eg benzyl) and Hal represent halo and Y represents IIa or IIb, alk² is as hereinabove defined, with a compound of formula ZH, in which Z is as hereinabove defined, for example in an inert organic liquid, eg tetrahydrofuran or $\underline{N},\underline{N}$-dimethylformamide, at a temperature in the range 0°–150° C. in the presence of a base, for example sodium hydride; preferably by heating at a temperature in the range 20°–150° C. It will be appreciated by those skilled in the art that this reaction may give rise to quaternary salt by-products, compounds of formula IX may be separated by known techniques eg, distillation. The protecting group (eg benzyl) may then be removed, for example by treatment with hydrogen in the presence of a catalyst such as palladium on charcoal, or by treatment with a mixture of palladium on charcoal and ammonium formate. In both reactions, preferably an inert organic liquid, eg ethanol, is employed at a temperature in the range 0°–200° C. Compounds of formula IX having a protecting group are specified herein as compounds of formula IXa.

A compound of formula X may be prepared by reacting a compound of formula XV in which alk¹ represents alk⁵ and b represents 1, with a compound of formula XVI, for example in an inert organic liquid, eg tetrahydrofuran, at a temperature in the range 0°–200° C. in the presence of a base, for example sodium hydride; preferably by heating at a temperature in the range 20°–150° C. It will be appreciated by those skilled in the art that this reaction may give rise to quaternary salt by-products, compounds of formula X may be separated by known techniques, eg distillation.

A compound of formula X in which k represents 0, and j represents 1 may also be prepared by hydrogenating a compound of formula XII in which b represents 1, alk¹ represents alk⁵ and R₁, R₂, R₃, y, Z, and alk³ are as hereinabove defined, for example by reaction with hydrogen in the presence of a catalyst such as palladium on charcoal and in the presence of an inert organic liquid such as ethanol at a pressure in the range 1–10 atmospheres.

A compound of formula XI in which Y represents IIa may be prepared by reacting a compound of formula XXI

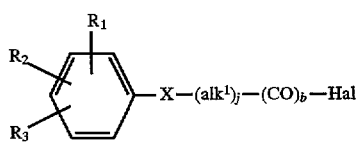

in which Hal represents halo, j represents 1 and R₁, R₂, R₃, X, alk¹ and b are as hereinabove defined with a compound of formula XXIa HY=O                                  XXIa in which Y represents IIa, for example in the presence of a base, eg triethylamine, in an inert organic liquid, eg dichloromethane, at a temperature in the range from 0° C. up to the boiling point of the inert organic liquid, eg 0°–50° C.

A compound of formula XIa may be prepared by reacting a compound of formula XXII $(C_2H_5O)_2P(=O)$—CHR$_8$-alk²-Hal        XXII where Hal represents halo, R₈ and alk² are as hereinabove defined with a compound of formula XVI in which Z is as hereinabove defined, for example by reaction in the presence of a base, eg sodium hydride, in an inert organic liquid, eg tetrahydrofuran, in the temperature range from 0° C. up to the boiling point of the inert organic liquid, eg 0°–200° C., preferably by heating at a temperature in the range 20°–150° C.

A compound of formula XII may be prepared by reacting a compound of formula XI with a Wittig reagent such as a compound of formula XXIIa $(C_2H_5O)_2P(=O)$—CHR$_8$-alk³-Z          XXIIa in which R₈, alk³ and Z are as hereinabove defined (which has been treated with a base, eg sodium hydride, in an inert organic liquid, eg tetrahydrofuran) at a temperature in the range 0°–200° C. in a suitable solvent; preferably by heating at a temperature in the range 20°–150° C.

A compound of formula XXIIa may be prepared from a compound of formula XXIII $(C_2H_5O)_2P(=O)$—CHR$_8$-alk³-Hal        XXIII in which Hal represents halo and R₈ and alk³ are as hereinabove defined, in a similar manner to that described for the preparation of a compound of formula XIa from a compound of formula XXII.

Compounds of formulae XIII, XIV and XVI may be prepared by methods known to those skilled in the art.

A compound of formula XV may be prepared by halogenating a compound of formula XXIV

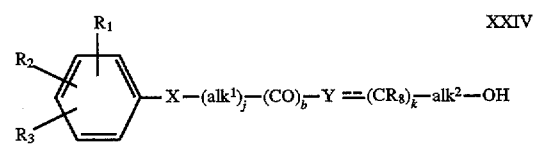

in which b, j and k are 0 or 1, X is other than —NHCO—, and R₁, R₂, R₃, alk¹, alk² and Y are as hereinabove defined, for example by reaction with thionyl chloride at a temperature in the range 0°–200° C., optionally in the presence of an inert organic liquid, eg chloroform; preferably by heating at a temperature in the range 20°–150° C.

A compound of formula XVII may be prepared by reacting a compound of formula XXV

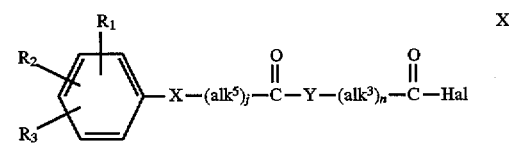

in which Hal represents halo, Y represents IIa or IIb and R₁, R₂, R₃, X, Y, alk⁵, alk³, j and n are as hereinabove defined, with a compound of formula XVI, for example by reaction in the presence of a base, eg triethylamine, in an inert organic liquid, eg tetrahydrofuran, in the temperature range from 0° C. up to the boiling point of the inert organic liquid, eg 0°–200° C., preferably by heating at a temperature in the range 20°–150° C.

A compound of formula XVIII in which Y represents IIa or IIb may be prepared by reacting a compound of formula XXVI HY-alk²-Z                              XXVI in which Y represents IIa or IIb, Z and alk² are as hereinabove defined, wish a compound of formula XXVII

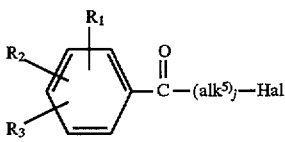
XXVII in which Hal represents halo and $R_1$, $R_2$, $R_3$, $alk^5$ and j are as hereinabove defined, for example by reaction in the presence of a base, eg triethylamine, in an inert organic solvent, eg toluene, ethanol or tetrahydrofuran, in the temperature range from 0° C. up to the boiling point of the inert organic liquid, eg 0°–200° C., preferably by heating at a temperature in the range 20°–150° C. It will be appreciated by those skilled in the art that this reaction may give rise to quaternary salt by-products, compounds of formula XVIII may be separated by known techniques, eg distillation.

Compounds of formula XIX, XXI, XXIa, XXII and XXIII may be prepared by methods known in the art.

A compound of formula XX may be prepared by reacting a compound of formula XXVIII

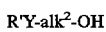
R'Y-alk²-OH    XXVIII in which R', Y and alk² are as hereinabove defined, for example by reaction with thionyl chloride at a temperature in the range 0°–200° C. with or without the presence of an inert organic liquid, eg chloroform, preferably by heating at a temperature in the range 20°–150° C.

A compound of formula XXIV may be prepared by reacting a compound of formula XXI with a compound of formula XXIX

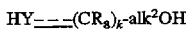
HY---(CR₈)ₖ-alk²OH    XXIX in which $R_8$, k, $alk^2$ and Y are as hereinabove defined, for example by reaction in the presence of a base, eg triethylamine, in an inert organic liquid, eg industrial methylated spirits or dichloromethane, at a temperature in the range from 0° C. up to the boiling point of the inert organic liquid, eg 0°–200° C., preferably by heating at a temperature in the range 20°–150° C.

A compound of formula XXV in which X is other than —NHCO—, may be prepared by halogenating a compound of formula XXX

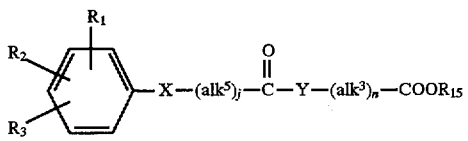
XXX in which X is other than —NHCO—, $R_{15}$ represents hydrogen and $R_1$, $R_2$, $R_3$, X, Y, $alk^5$, $alk^3$, j and n are as hereinabove defined, for example by reaction with thionyl chloride an a temperature in the range 0°–200° C., optionally in the presence of an inert organic liquid, eg chloroform; preferably by heating at a temperature in the range 20°–150° C.

A compound of formula XXVI may be prepared from a compound of formula X where k is 0 in the same manner as is prepared a compound of formula IX.

A compound of formula XXVII may be prepared by methods known to those skilled in the art.

A compound of formula XXVIII may be prepared by reducing a compound of formula XXXI

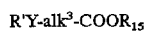
R'Y-alk³-COOR₁₅    XXXI in which $R_{15}$ represents hydrogen or $C_{1-4}$ alkyl and R' and $alk^3$ are as hereinabove defined, for example by treatment with a reducing agent, such as lithium triethylborohydride in the presence of an inert organic liquid, eg tetrahydrofuran, at a temperature in the range −10° to 50° C. The protecting group R' (eg benzyl) may then be removed, for example by treatment with hydrogen in the presence of a catalyst such as palladium on charcoal or by treatment with a mixture of palladium on charcoal and ammonium formate. In both reactions, a temperature in the range 0°–200° C. and preferably an inert organic liquid, eg ethanol, is employed.

A compound of formula XXIX in which k is 0 may be prepared by reducing a compound of formula XXXI in which R' represents hydrogen and $R_{15}$ and $alk^3$ are as hereinabove defined, for example by treatment with a reducing agent, such as lithium triethylborohydride in an inert organic liquid, eg tetrahydrofuran, at a temperature in the range −10° to 50° C.

A compound of formula XXX in which n is 1 may be prepared by reacting a compound of formula XXI in which $alk^1$ represents $alk^5$ and b represents 1 with a compound of formula XXXI in which R' represents hydrogen, $R_{15}$ represents hydrogen or $C_{1-4}$ alkyl and Y and $alk^3$ are as hereinbefore defined, in the presence of a base, eg triethylamine, in an inert organic liquid, eg methylene chloride, at a temperature in the range from 0° C. up to the boiling point of the inert organic liquid, eg 0°–200° C. (preferably by heating at a temperature in the range 20°–150° C.)

A compound of formula XXXI may be prepared by hydrogenating a compound of formula XXXII

R'Y=CR₈alk⁶-COOR₁₅    XXXII in which $alk^6$ is $C_{1-4}$ alkylene, optionally substituted by one or more $C_{1-4}$ alkyl groups, and R', Y, $R_8$ and $R_{15}$ are as hereinabove defined, for example by reaction with hydrogen in the presence of a catalyst such as palladium on charcoal or platinum oxide and in the presence of an inert organic liquid such as ethanol at a pressure in the range 1–10 atmospheres.

A compound of formula XXXII may be prepared by reacting a compound of XXXIII

R'Y=O    XXXIII in which R' is as hereinabove defined with a Wittig reagent such as a compound of formula XXXIV

(C₂H₅O)₂P(=O)—CHR₈-alk⁶-COOR₁₅    XXXIV in which $alk^6$, $R_8$ and $R_{15}$ are as hereinabove defined (which reagent has been treated with a base, eg sodium hydride in an inert organic liquid, eg tetrahydrofuran) at a temperature in the range from 0° C. to the boiling point of the inert organic liquid, eg 0°14 200° C., preferably by heating to a temperature in the range 20°–150° C.

Compounds of formula XXXIII to XXXIV may be prepared by methods known to those skilled in the art.

It will be appreciated by those skilled in the art that when either or both chains -alk¹-(CO)b— and ---(CR₈)ₖ-alk²- are connected to carbon atoms in the ring Y, then the free nitrogen atom or atoms in ring Y may be protected by a protecting group, eg benzyl or benzoyl which may be removed at an appropriate stage in the process, for example in the final stage.

The substituents specified for $R_1$, $R_2$ and $R_3$ in compounds of formula I may interconverted by methods known to those skilled in the art. The substituents specified for $R_9$ and $R_{10}$ in groups of formula II may be interconverted by methods known to those skilled in the art. The substituents specified for $R_{11}$, $R_{12}$, $R_{13}$ and $R_{14}$ in groups of formula V may be interconverted by methods known to those skilled in the art.

Certain intermediate compounds of formula VIII, IX, X, XI, XIa, XII, XIIa, XV, XVII, XVIII, XX, XXIV, XXV, and XXVIII–XXXIV are believed to be novel compounds. All novel compounds herein are claimed as a further aspect of the invention.

The invention is illustrated by the following nonlimitative Examples. In the Examples parts and percentages are by weight and compositions of mixed solvents are given by volume. Characterisation was by elemental analysis and one or more of the following spectroscopic techniques: nuclear magnetic resonance, infra-red and mass spectroscopy.

EXAMPLE 1 a) Lithium triethylborohydride (100 ml, 1M solution in tetrahydrofuran) was added dropwise to a solution of ethyl 1-benzoyl-4-piperidineacetate (13.8 g) in dry tetrahydrofuran (50 ml) at 0° C. under nitrogen over 20 minutes whilst maintaining the temperature at 0°–5° C. The mixture was stirred at 0° C. for a further hour, allowed to warm to 20° C. and then water (50 ml) was added slowly. The mixture was acidified with a slight excess of dilute hydrochloric acid and extracted with ethyl acetate. The combined ethyl acetate extracts were washed (dilute hydrochloric acid, brine), dried and evaporated to give 1-benzoyl-4-(2-hydroxyethyl) piperidine as an oil.

b) A mixture of the product from part (a) (1.0 g) in chloroform (10 ml) was treated dropwise with thionyl chloride (0.4 ml) and stirred at 20° C. for 1 hour. After heating under reflux for 30 minutes the mixture was evaporated to dryness, the residue was dissolved in dichloromethane, washed (sodium bicarbonate solution, brine), then dried and evaporated to give 1-benzoyl-4-(2-chloroethyl)piperidine as an oil.

EXAMPLE 2

(a) A solution of triethyl 2-phosphonopropionate (50.0 g) in dry tetrahydrofuran (75 ml) was added dropwise to a stirred suspension of sodium hydride (60% in mineral oil, 8.0 g) in dry tetrahydrofuran (275 ml) under nitrogen and stirred at 20° C. for 10 minutes until a clear solution was formed. 1-Benzoyl-4-piperidone (34.5 g) in dry tetrahydrofuran (75 ml) was added dropwise to the clear solution and the reaction mixture heated under reflux for 16 hours. After quenching the reaction mixture with 5M hydrochloric acid (20 ml), the resulting solid was removed by filtration. Excess ether was added to the filtrate, the aqueous layer separated off and the ethereal layer washed (water), dried, filtered and concentrated to give ethyl 2-(1-benzoyl-4-piperidylidene) propionate as an oil.

(b) A solution of the product from part (a) (43.6 g) in ethanol (300 ml) was hydrogenated in the presence of platinum oxide (1.5 g) under hydrogen for 15 hours. The reaction mixture was then filtered and the filtrate was concentrated to give ethyl 2-(1-benzoyl-4-piperidinyl) propionate as an oil.

(c) Lithium triethylborohydride (200 ml, 1M solution in tetrahydrofuran) was added dropwise to a solution of the product from part (b) (28.9 g) in dry tetrahydrofuran (100 ml) cooled to −5° C. with stirring under nitrogen. The reaction mixture was stirred at −5° C. for 1 hour and then water (50 ml) added slowly. After pouring the reaction mixture onto water (200 ml) and acidifying to pH 6 with 2M hydrochloric acid, the layers were separated and the aqueous layer extracted with ethyl acetate. The combined organic layers were washed (2M hydrochloric acid, brine), dried, filtered and concentrated to give 1-benzoyl-4-(2-hydroxy-1-methylethyl)piperidine as an oil.

(d) Thionyl chloride (4.3 ml) was added dropwise to a solution of the product from part (c) (12.0 g) in chloroform (120 ml). The reaction mixture was stirred at 20° C. for 2 hours, heated under reflux for 1 hour and then allowed to cool to 20° C. and stood for 16 hours. The reaction mixture was concentrated, dissolved in dry dichloromethane, washed (sodium bicarbonate solution, brine), dried, filtered and concentrated to give 1-benzoyl-4-(2-chloro-1-methylethyl) piperidine as an oil.

EXAMPLE 3

A solution of oxalyl chloride (5 ml) in dichloromethane (5 ml) was added dropwise to a solution of 3-(4-methylphenyl) propionic acid (1.5 g) in dichloromethane (20 ml). The mixture was stirred at 20° C. for 16 hours and then evaporated to give 3-(4-methylphenyl)propionyl chloride as an oil.

EXAMPLES 4–9

In a similar manner to that described in Example 3, compounds of formula VIII were prepared by reacting compounds of formula XIX with a halogenating agent as shown in Table 1 below. In compounds of formula XIX, $R_3$ represents hydrogen, b represents 1 and $R_1$, $R_2$, X and $alk^1$ are as defined in Table 1.

The products were used directly in the next stage.

TABLE 1

| | Compound XIX | | | | | Halogenating Agent | | |
|---|---|---|---|---|---|---|---|---|
| Example | $R_1$ | X | $R_2$ | $alk^1$ | Amount (g) | | Amount (ml) | Notes |
| 4 | H | — | 4-Cl | $(CH_2)_2$ | 1.9 | Thionyl chloride | 4.0 | 1 |
| 5 | H | — | 4-OCH$_3$ | $(CH_2)_2$ | 1.7 | Oxalyl chloride | 5.0 | 2 |
| 6 | tetramethylene | | H | — | 1.1 | Oxalyl chloride | 5.0 | 2 |
| 7 | H | — | H | $CH(CH_3)CH_2$ | 1.4 | Oxalyl chloride | 5.0 | 2 |
| 8 | H | — | 4-SCH$_3$ | $(CH_2)_2$ | 1.8 | Oxalyl chloride | 5.0 | 2 |
| 9 | H | — | H | $(CH_2)_3$ | 3.3 | Oxalyl chloride | 11.0 | 2 |

Notes

1. Reaction mixture was heated under reflux with neat halogenating agent for 2 hours. Excess halogenating agent was distilled off by azeotroping with toluene.
2. Compound XIX treated with 0.2 ml N,N-dimethylformamide prior to addition of halogenating agent.

The compounds prepared in the Examples 4–9 were oily products named as follows:

Ex 4: 3-(4-Chlorophenyl)propionyl chloride
Ex 5: 3-(4-Methoxyphenyl)propionyl chloride
Ex 6: 1,2,3,4-tetrahydro-2-naphthoyl chloride
Ex 7: 3-Phenylbutyroyl chloride
Ex 8: 3-(4-Methylthiophenyl)propionyl chloride
Ex 9: 4-Phenylbutyroyl chloride

EXAMPLE 10

(a) A solution of imidazole (5.4 g) in dry N,N-dimethylformamide (50 ml) was added dropwise with stirring to a mixture of sodium hydride (3.2 g, 60% dispersion in mineral oil) in dry N,N-dimethylformamide (80 ml) under nitrogen. The mixture was stirred at 20° C. until evolution of hydrogen ceased. A solution of the product from Example 1 (20.0 g) in dry N,N-dimethylformamide (20 ml) was then added dropwise with stirring. The mixture was heated at 80°–100° C. for 16 hours and then the mixture was cooled and poured onto water (1l), then extracted with dichloromethane. The combined dichloromethane extracts were washed (water).

(b) The extracts were then extracted with 2M hydrochloric acid. After washing (dichloromethane), the acidic layer contained 1-benzoyl-4-[2-(imidazol-1-yl)ethyl]piperidine as an oil.

EXAMPLES 11–19

In a similar manner to that described in Example 10(a) compounds of formula IXa were prepared by reacting compounds of formula XX with compounds of formula XVI (treated with sodium hydride as described above) as shown in Table 2 below.

When compounds of formula XX are known in the art, R' is benzoyl, Y is a group of formula IIIa as hereinabove defined (in which $R_9$ is hydrogen) and $alk^2$ is as defined in Table 2 below. When compounds of formula XX are novel intermediates, their preparative Example is given.

In compounds of formula XVI, Z is as defined in Table 2 in terms of groups V(a)–(h) (with substituents $R_{11}$–$R_{14}$) as hereinabove defined.

Notes (1) The oil produced was dried and the resulting solid triturated with ether to give the solid product.
(2) Mixture of products was separated by flash chromatography (eluting with ethyl acetate/triethylamine (9:1)) to give an oily product.
(3) Unseparated mixture of isomers.
(4) Purified by column chromatography eluting with methanol/dichloromethane (1:49) on silica and then further eluting with methanol/dichloromethane (1:24).

The compounds prepared in Examples 11–19 were as follows:

Ex 11: 1-Benzoyl-4-[2-(imidazol-1-yl)-1-methylethyl]piperidine
Ex 12: 1-{2-(1-Benzoylpiperidin-4-yl)ethyl}benzimidazole
Ex 13: 1-Benzoyl-4-[2-(4,5-dichloro-2-methylimidazol-1-yl)ethyl]piperidine
Ex 14: 1-Benzoyl-4-[2-(4,5-dimethylimidazol-1-yl)ethyl]piperidine
Ex 15: 1-Benzoyl-4-[2-(2-methylimidazol-1-yl)ethyl]piperidine
Ex 16: 1-Benzoyl-4-[2-(4-methylimidazol-1-yl)ethyl]piperidine and 1-Benzoyl-4-[2-(5-methylimidazol-1-yl)ethyl]piperidine
Ex 17: (a) 1-Benzoyl-4-[2-(1H-1,2,3-triazol-1-yl)ethyl]piperidine and (b) 1-Benzoyl-4-[2-(2H-1,2,3-triazol-2-yl)ethyl]piperidine
Ex 18: 1-Benzoyl-4-[2-(2H-tetrazol-2-yl)ethyl]piperidine
Ex 19: 4-{2-[2-(2-Chlorobenzoyl)imidazol-1-yl]ethyl}-1-(3-phenylpropionyl)piperidine

EXAMPLE 20

6M Hydrochloric acid (150 ml) was added to the combined acid extracts from Example 10 and the solution heated at 80°–100° C. for 16 hours. The reaction mixture was cooled and washed with dichloromethane. The acidic layer was concentrated, basified with 2M sodium hydroxide solution and extracted with dichloromethane. The extracts were dried, filtered and evaporated to give 4-[2-(imidazol-1-yl)ethyl]piperidine as an oil.

EXAMPLES 21–31

In a similar manner to that described in Example 20, compounds of formula IX were prepared by treatment of compounds of formula IXa with 6M hydrochloric acid as

TABLE 2

| Ex | Compound XX alk² | Amt (g) | Compound XVI Group Z | $R_{11}$ | $R_{12}$ | $R_{13}$ | $R_{14}$ | Amt (g) | Reaction Time (hrs) | Compound IXa m. pt °C. | Notes |
|---|---|---|---|---|---|---|---|---|---|---|---|
| 11 | Prep Ex 2 | 1.0 | Va | H | H | H | — | 0.3 | 4.75 | Oil | |
| 12 | (CH₂)₂ | 0.5 | Vh | H | — | — | H | 0.2 | 3.15 | 116–118 | 1 |
| 13 | (CH₂)₂ | 1.0 | Va | Cl | Cl | CH₃ | — | 0.6 | 5.0 | Oil | |
| 14 | (CH₂)₂ | 4.3 | Va | CH₃ | CH₃ | H | — | 2.3 | 5.0 | Oil | |
| 15 | (CH₂)₂ | 1.0 | Va | H | H | CH₃ | — | 0.3 | 4.75 | Waxy Solid | |
| 16 | (CH₂)₂ | 7.0 | Va | H | CH₃ | H | — | 2.3 | 5.0 | Oil | 3 |
| 17 | (CH₂)₂ | 4.0 | Vf | H | H | — | — | 1.1 | 3.0 | Oil | 2 |
| 18 | (CH₂)₂ | 2.5 | Vd | H | — | — | — | 0.7 | 2.5 | 135–139 | 2, 1 |
| 19 | (CH₂)₂ | 4.1 | Va | H | H | 2-Cl-benzoyl | — | 3.0 | 5.0 | Oil | 4 | shown in Table 3 below. The preparative Example for compounds of formula IXa is given in Table 3 below:

TABLE 3

| Example | Compound IXa Preparative Example | Hydro-chloric Acid Amount (ml) | Reaction Time (hrs) | Compound IX m. pt (°C.) | Notes |
|---|---|---|---|---|---|
| | | Amount (g) | | | |
| 21 | 11 | 11.3 | 120 | 16.0 | Oil | |
| 22 | 12 | 2.0 | 31 | 18.0 | 217 (dec) | 1 |
| 23 | 13 | 3.3 | 35 | 16.0 | Oil | |
| 24 | 14 | 4.4 | 50 | 16.0 | Oil | |
| 25 | 15 | 1.0 | 20 | 16.0 | Oil | |
| 26 | 16 | 5.6 | 70 | 16.0 | Oil | 2 |
| 27 | 17 (a) | 2.3 | 23 | 16.0 | 87–89 | |
| 28 | 17 (b) | 3.8 | 38 | 16.0 | 60–62 | 1 |
| 29 | 18 | 3.2 | 23 | 16.0 | Oil | |
| 30 | 67 | 5.9 | 130 | 16.0 | Oil | |
| 31 | 19 | 0.5 | 30 | 24.0 | Oil | |

N.B. (dec) = with decomposition

Notes
(1) Resulting residue was triturated with ether to give solid product.
(2) Unseparated mixture of products.

The compounds prepared in Examples 21–30 were as follows:

Ex 21: 4-[2-(imidazol-1-yl)-1-methylethyl]-piperidine
Ex 22: 1-[2-(piperidin-4-yl)ethyl]benzimidazole
Ex 23: 4-[2-(4,5-dichloro-2-methylimidazol-1-yl)ethyl]piperidine
Ex 24: 4-[2-(4,5-dimethylimidazol-1-yl)ethyl]piperidine
Ex 25: 4-[2-(2-methylimidazol-1-yl)ethyl]piperidine
Ex 26: 4-[2-(5-methylimidazol-1-yl)ethyl]piperidine and 4-[2-(4-methylimidazol-1-yl)ethyl]piperidine
Ex 27: 4-[2-(1H-1,2,3-triazol-1-yl)ethyl]piperidine
Ex 28: 4-[2-(2H-1,2,3-triazol-2-yl)ethyl]piperidine
Ex 29: 4-[2-(2H-tetrazol-2-yl)ethyl]piperidine
Ex 30: 4-[2-(2-methylimidazol-1-yl)ethyl]piperidine
Ex 31: 4-{2-[2-(2-Chlorobenzoyl)imidazol-1-yl]ethyl}piperidine

EXAMPLE 32

(a) Triethyl phosphonoacetate (1.1 ml) was added to a solution of sodium (0.1 g) in absolute ethanol (5 ml) and stirred at 20° C. for 0.25 hours. A solution of 1-benzyl-3-methylpiperidone (1.0 g) in ethanol (1 ml) was added dropwise to the reaction mixture. The reaction mixture was stirred for 1 hour, whilst maintaining the temperature at 20° C. After standing for 16 hours the reaction mixture was poured onto brine and extracted with ether. The combined organic extracts were washed (water), dried and evaporated to give ethyl 1-benzyl-3-methyl-4-piperidylideneacetate admixed with ethyl 1-benzyl-3-methyl-1,2,3,6-tetrahydro-4-pyridineacetate and ethyl 1-benzyl-5-methyl-1,2,3,6-tetrahydro-4-pyridine acetate.

(b) A solution of the product from part (a) (31.6 g) in absolute ethanol (300 ml) containing platinum oxide (0.5 g) was stirred vigorously under a hydrogen atmosphere. The reaction mixture was filtered, the insolubles washed (ethanol) and the filtrate evaporated to give ethyl 1-benzyl-3-methyl-4-piperidineacetate as an oil.

(c) Lithium triethylborohydride (110 ml, 1M solution in tetrahydrofuran) was added dropwise over 0.5 hour under nitrogen with stirring to a solution of the product from part (b) (15.0 g) in dry tetrahydrofuran (100 ml) cooled to −5° C. The reaction mixture was stirred at 0° C. for 2 hours then water (50 ml) was added dropwise. After adding a further portion of water (200 ml), 2M hydrochloric acid was added until the pH of the reaction mixture was 6. The aqueous layer was separated off and extracted with ether. The combined organic extracts were washed (2M hydrochloric acid, brine), dried and evaporated to give 1-benzyl-4-(2-hydroxyethyl)-3-methylpiperidine as an oil.

(d) A stirred solution of the product from part (c) (100 mg) in absolute ethanol (10 ml) under nitrogen was treated with palladium on wet charcoal (10%, 0.3 g) followed by ammonium formate (0.2 g). The reaction mixture was heated under reflux for 1 hour under nitrogen, then hot filtered through Celite®, washed (ethanol) and evaporated to give 4-(2-hydroxyethyl)-3-methylpiperidine as an oil.

EXAMPLE 33

(a) Triethyl phosphonoacetate (17 ml) was added to a solution of sodium (4.5 g) in absolute ethanol (180 ml) and stirred at 20° C. for 0.5 hours. A solution of 1-benzyl-3-piperidone (19 g) in ethanol (100 ml) was added dropwise to the reaction mixture. The reaction mixture was stirred for 16 hours at 20° C. and then was poured onto brine and extracted with ether. The combined organic extracts were washed (water), dried, filtered and concentrated to given an oily product which was purified by elution with dichloromethane through a Florisil® column to give ethyl 1-benzyl-3-piperidylideneacetate as an oil.

(b) A solution of the product from part (a) (6.0 g) in ethyl acetate (75 ml) containing platinum oxide (0.5 g) was stirred vigorously under a hydrogen atmosphere for 14 hours. The reaction mixture was filtered through Celite® and the filtrate evaporated to give ethyl 1-benzyl-3-piperidineacetate as an oil.

(c) Lithium triethylborohydride (46 ml, 1M solution in tetrahydrofuran) was added dropwise over 0.5 hour to a solution of the product from part (b) (5.9 g) in dry tetrahydrofuran (23 ml), cooled to −8° C. with stirring under nitrogen. The reaction mixture was stirred at −4° C. for 3 hours then water (12 ml) added. The reaction mixture was added to a further portion of water (46 ml) and to this mixture 2M hydrochloric acid was added until the pH of the reaction mixture was 7. The aqueous layer was separated off and extracted with dichloromethane. The combined organic extracts were washed (2M hydrochloric acid, brine), dried, filtered and concentrated to give 1-benzyl-3-(2-hydroxyethyl)piperidine as an oil.

(d) A stirred solution of the product from part (c) (2.8 g) in absolute ethanol (100 ml) was treated with palladium on charcoal (10%, 3.8 g) followed by ammonium formate (3.6 g). The reaction mixture was heated under reflux for 1 hour under nitrogen then hot filtered through Celite®, washed (ethanol) and evaporated to give 3-(2-hydroxyethyl)piperidine as an oil.

EXAMPLE 34

(a) A solution of the product from Example 38 (14.7 g) in dichloromethane (100 ml) was added to a stirred suspension of pyridinium chlorochromate (19.1 g) in dichloromethane (400 ml) and the reaction mixture stirred at 20° C. for 5 hours. Ether (300 ml) was then added to the reaction mixture. The solution was decanted off and the solid was washed with more ether (300 ml). The combined organic extracts were purified by gradient chromatography, eluting with dichloromethane/ether (1:1) on a Florisil® column and then concentrating the eluant to give 1-(3-phenylpropionyl)-4-piperidinecarboxaldehyde as an oil.

(b) A solution of triethyl phosphonoacetate (8 ml) in dry tetrahydrofuran (47 ml) was added dropwise to a stirred suspension of sodium hydride (60% in mineral oil, 1.6 g) in dry tetrahydrofuran (240 ml) under nitrogen and stirred for 1.75 hours. A solution of the product from part (a) (9.5 g) in dry tetrahydrofuran (47 ml) was added dropwise to the reaction mixture, followed by stirring at 20° C. for 16 hours. The reaction mixture was treated dropwise with 1M hydrochloric acid (200 ml) and extracted with ether. The combined ether extracts were washed (water, saturated sodium bicarbonate solution), dried and evaporated to give ethyl 3-[1-3-phenylpropionyl)piperidin-4-yl]propenoate as an oil.

(c) A solution of the product from part (b) (8.0 g) in ethanol (60 ml) was treated with platinum oxide (0.3 g) and stirred at 20° C. under a hydrogen atmosphere for 2 hours. The reaction mixture was filtered and the filtrate evaporated to give ethyl 3-[1-(3-phenylpropionyl)piperidin-4-yl]propionate as an oil.

(d) A solution of lithium triethylborohydride in tetrahydrofuran (10 ml, 1M) was added dropwise to a cooled solution of the product from part (c) (1.4 g) in dry tetrahydrofuran (10 ml) under a nitrogen atmosphere. The reaction mixture was stirred for 3 hours, maintaining the temperature below 5° C., and then water (20 ml) added dropwise. 2M Hydrochloric acid was added until the pH of the reaction mixture was 5–6. The aqueous layer was extracted with ethyl acetate. The combined organic extracts were dried and evaporated. Purification by flash chromatography, eluting with ethyl acetate/triethylamine (9:1), gave 1-(3-phenylpropionyl)-4(3-hydroxypropyl)piperidine as an oil.

EXAMPLE 35

A mixture of 3-phenylpropionic acid (29.5 g) and thionyl chloride (35 ml) in dry toluene (100 ml) was heated under reflux at 80°–100° C. for two hours. The mixture was then evaporated. The residue was treated with two portions of toluene and the resultant solution was evaporated on each occasion yielding an oil which was then dissolved in dry dichloromethane (50 ml). The solution was added dropwise to a stirred solution of 4-piperidine-ethanol (25.2 g) and triethylamine (22.2 g) in dichloromethane (250 ml) at 0° C. over one hour, maintaining the temperature at 0° C. The mixture was allowed to warm to 20° C. and was stirred for 18 hours and then washed with saturated sodium bicarbonate solution. The organic layer was separated and evaporated to dryness. The residue was dissolved in dioxan (20 ml) and 1M sodium hydroxide solution (20 ml) was then added. The solution was stirred at 20° C. for 20 hours and then stirred at 40° C. for a further 4 hours. The solution was evaporated and the residue treated with dilute sodium hydroxide solution and then extracted with ethyl acetate. The combined ethyl acetate extracts were washed (dilute hydrochloric acid, brine), dried and evaporated to give 4-(2-hydroxyethyl)-1-(3-phenylpropionyl)piperidine as an oil.

EXAMPLE 36

A mixture of 3-phenylpropionic acid (11.6 g) and thionyl chloride (15 ml) was heated under reflux for 2 hours. Excess thionyl chloride was distilled off under reduced pressure, azeotroping with toluene. The resulting 3-phenylpropionyl chloride was dissolved in dichloromethane (20 ml) and was added dropwise to a stirred solution of 2-piperidineethanol (10.0 g) and triethylamine (11.8 ml) in dichloromethane (95 ml) at 0° C. over 1.5 hours. The reaction mixture was stirred for 16 hours at 20° C. and then washed (saturated sodium bicarbonate solution, water), dried and evaporated. The residue was dissolved in dioxan (10 ml) and treated with 1M sodium hydroxide solution. After standing for 24 hours the solution was evaporated and the residue treated with dilute sodium hydroxide solution. After extraction with ethyl acetate the combined organic extracts were washed (dilute hydrochloric acid), dried and evaporated to give 2-(2-hydroxyethyl)-1-(3-phenylpropionyl)piperidine as an oil.

EXAMPLE 37

A solution of 3-phenylpropionyl chloride (29.7 ml) in dichloromethane (100 ml) was added dropwise to a stirred solution of 3-piperidinemethanol (23 g) and triethylamine (22.2 g) in dichloromethane (200 ml) at 0° C. over 1.25 hours, maintaining the temperature at 0° C. The mixture was stirred at 0°–5° C. for 22 hours. After washing (saturated sodium bicarbonate solution), the organic layer was separated off, dried and evaporated to give 3-hydroxymethyl-1-(3-phenylpropionyl)piperidine as an oil.

EXAMPLES 38–40

In a similar manner to that described in Example 37, compounds of formula XXIX were reacted with a compound of formula XXI to give compounds of formula XXIV as shown in Table 4 below.

The compound of formula XXI is known in the art: $R_1$, $R_2$ and $R_3$ are hydrogen, X is a bond, $alk^1$ is —$(CH_2)_2$—, j and b are 1 and Hal is chloro.

For the compound of formula XXIX known in the art, $alk^2$ is $CH_2$, Y is defined by a group of formula III(a), $R_9$ is hydrogen and is represented in Table 4 by XXIX(I). When compounds of formula XXIX are novel intermediates, the preparative details are given in Table 4 below.

TABLE 4

| | Compound XXIX | | Compound XXI | Et$_3$N | Reaction Time | Compound XXIV | |
|---|---|---|---|---|---|---|---|
| Example | Structure | Amount (g) | Amount (g) | Amount (ml) | (hours) | m. pt °C. | Notes |
| 38 | XXIX(I) | 2.7 | 4.0 | 2.6 g | 18 | Oil | 1a |
| 39 | Preparative Example 32d | 2.2 | 2.2 | 2.3 | 18 | Oil | 2 |
| 40 | Preparative Example 33d | 1.4 | 1.6 ml | 1.7 | 18 | Oil | 1b |

Notes (1) Purification by column chromatography eluting with (a) dichloromethane/methanol (19:1);

(b) dichloromethane/methanol (9:1) on silica gel gave an oily product

The preparative Examples for each compound of formula XXIV is given in Table 5.

TABLE 5

| | | | | Reaction Time | | |
| | Compound XXIV | | | Stirring | Reflux | Compound |
| Example | Preparative Example | Amount (g) | SOCl$_2$ Amount (ml) | Time at 20° C. (hours) | Time (hours) | XV m. pt °C. |
| --- | --- | --- | --- | --- | --- | --- |
| 43 | 36 | 3 | 0.9 | — | 2.5 | Oil |
| 44 | 37 | 15.1 | 5.0 | 1.0 | 5.0 | Oil |
| 45 | 38 | 4.1 | 2.2 g | 0.5 | 2.5 | Oil |
| 46 | 39 | 2.4 | 0.8 | — | 2.0 | Oil |
| 47 | 40 | 1.1 | 0.4 | 2.0 | 1.0 | Oil |
| 48 | 41 | 7.8 | 2.1 | 1.75 | 2.5 | Oil |
| 49 | 34d | 2.0 | 0.6 | 1.5 | 2.5 | Oil |

(2) The residue was dissolved in dioxan, treated with 1M sodium hydroxide solution. On evaporation, the residue was partitioned between 1M sodium hydroxide solution and ethyl acetate and the aqueous liquors were extracted with ethyl acetate and the combined organic liquors washed (water), dried and evaporated.

In Examples 38–40 the compounds prepared were as follows:

Ex 38: 4-Hydroxymethyl-1-(3-phenylpropionyl)piperidine
Ex 39: 4-(2-Hydroxyethyl)-3-methyl-1-(3-phenylpropionyl) piperidine
Ex 40: 3-(2-Hydroxyethyl)-1-(3-phenylpropionyl)piperidine

EXAMPLE 41

A solution of oxalyl chloride (25 ml) in dichloromethane (20 ml) was added carefully to a solution of 3-(4-chlorophenyl)propionic acid (6.0 g) and N,N-dimethylformamide (0.3 ml) in dichloromethane (50 ml) and the reaction mixture stirred for 16 hours at 20° C. The reaction mixture was evaporated and the resulting foam dissolved in dichloromethane (20 ml) and added to a stirred solution of 4-(2-hydroxyethyl)piperidine (4.2 g) and triethylamine (5 ml) in dichloromethane (20 ml) at 0° C. The reaction mixture was stirred for 16 hours at 20° C., then washed (saturated sodium bicarbonate solution, water), dried and evaporated to give 1-[3-(4-chlorophenyl) propionyl]-4-(2-hydroxyethyl)piperidine, m.p. 88°–90° C.

EXAMPLE 42

A solution of thionyl chloride (15.7 ml) in dry chloroform (100 ml) was added dropwise to a stirred solution of the product from Example 35 (51.1 g) in dry chloroform (500 ml) over 45 minutes, keeping the temperature between 0° C. and 5° C. The solution was allowed to warm to 20° C. with stirring and then heated under reflux for 2.5 hours. The mixture was cooled to 20° C., washed (saturated sodium bicarbonate solution, water), dried, filtered and evaporated to give 4-(2-chloroethyl)-1-(3-phenylpropionyl)piperidine as oil.

EXAMPLES 43–49

In a similar manner to that described in Example 42, compounds of formula XV were prepared by reacting compounds of formula XXIV with thionyl chloride as a halogenating agent as shown in Table 5 below.

In Examples 43–49 the compounds prepared were as follows:

Ex 43: 2-(2-Chloroethyl)-1-(3-phenylpropionyl)piperidine
Ex 44: 3-Chloromethyl-1-(3-phenylpropionyl)piperidine
Ex 45: 4-Chloromethyl-1-(3-phenylpropionyl)piperidine
Ex 46: 4-(2-Chloroethyl)-3-methyl-1-(3-phenylpropionyl) piperidine
Ex 47: 3-(2-Chloroethyl)-1-(3-phenylpropionyl)piperidine
Ex 48: 4-(2-Chloroethyl)-1-[3-(4-chlorophenyl)propionyl] piperidine
Ex 49: 4-(3-Chloropropyl -1-(3-phenylpropionyl)piperidine

EXAMPLE 50

A solution of imidazole (1.4 g) in dry tetrahydrofuran (20 ml) was added dropwise with stirring to a mixture of sodium hydride (0.8 g, 60% dispersion in mineral oil) in tetrahydrofuran (20 ml) under nitrogen. The mixture was stirred at 20° C. for 3 hours and then a solution of the product from Example 42 (5.6 g) in dry tetrahydrofuran (50 ml) was added dropwise with stirring. The mixture was heated under reflux for 9 hours and then cooled to 20° C. Water (50 ml) was added and the solution stirred for 10 minutes. The mixture was basified with dilute sodium hydroxide solution and extracted with dichloromethane. The combined dichloromethane extracts were washed (water), dried and filtered before evaporation to give 4-[2-(imidazol-1-yl)ethyl]-1-(3-phenylpropionyl)piperidine as an oil.

EXAMPLE 51

A solution of imidazole (0.2 g) in dry N,N-dimethylformamide (10 ml) was added dropwise with stirring to a mixture of sodium hydride (0.2 g, 60% dispersion in mineral oil) in dry N,N-dimethylformamide (4 ml). The reaction mixture was stirred at room temperature under nitrogen for two hours. A solution of the product from Example 47 (0.8 g) in dry N,N-dimethylformamide (10 ml) was added dropwise with stirring and the reaction mixture heated at 80°–100° C. for 5 hours then allowed to cool to ambient temperature under a nitrogen atmosphere. The reaction mixture was poured into water (40 ml) and extracted with dichloromethane. The organic extracts were combined, washed (water), dried, filtered and concentrated to give 3-[2-(imidazol-1-yl)ethyl]-1-(3-phenylpropionyl) piperidine as an oil.

EXAMPLE 52–57

In a similar manner to that described in Example 51, compounds of formula X were prepared by reacting compounds of formula XV with compounds of formula XVI as shown in Table 6 below.

Compounds of formula XV are novel intermediates and their preparative Example are defined in Table 6 below. Compounds of formula XVI, are known in the art: Z is defined in Table 6 as Group V (a) (with substituents $R_{11}$, $R_{12}$, $R_{13}$ and $R_{14}$) as hereinabove defined.

The compounds prepared in Examples 52–57 were as follows:

Ex 52: 2-[2-(Imidazol-1-yl)ethyl]-1-(3-phenylpropionyl)piperidine dihydrochloride
Ex 53: 3-Imidazol-1-ylmethyl-1-(3-phenylpropionyl)piperidine
Ex 54: 4-Imidazol-1-ylmethyl-1-(3-phenylpropionyl)piperidine
Ex 55: 4-[2-(Imidazol-1-yl)ethyl]-3-methyl-1-(3-phenylpropionyl)piperidine

TABLE 6

|    | Compound XV |       | Compound XVI |          |          |          |          |          | NaH      | R. Time | Compound X |       |
|----|-------------|-------|--------------|----------|----------|----------|----------|----------|----------|---------|------------|-------|
| Ex | Prep. Ex    | Amt. (g) | Group Z   | $R_{11}$ | $R_{12}$ | $R_{13}$ | $R_{14}$ | Amt. (g) | Amt. (g) | (hrs)   | m.p. °C.   | Notes |
| 52 | 43 | 0.7 | Va | H | H | H | —   | 0.3 | 0.1 |    | 148–151 | 1, 2 |
| 53 | 44 | 4.0 | Va | H | H | H | —   | 1.0 | 1.3 | 6  | Oil     | 3    |
| 54 | 45 | 3.2 | Va | H | H | H | —   | 1.5 | 1.6 | 18 | Oil     | 5    |
| 55 | 46 | 1.8 | Va | H | H | H | —   | 0.4 | 0.4 | 5  | Oil     |      |
| 56 | 49 | 2.1 | Va | H | H | H | —   | 0.5 | 0.5 | 5  | 58–64   | 3    |
| 57 | 48 | 3.5 | Va | H | H | $CH_3$ | — | 0.9 | 0.8 | 4  | Oil     | 4    |

Ex = Example
R. Time = Reaction Time
Amt. = Amount

Notes
(1) Reaction conditions and purification as in Example 50.
(2) The oily product was dissolved in absolute ethanol and treated with ethereal hydrogen chloride. On cooling the solid produced with scratching was collected by filtration, washed (ether) and dried.
(3) The organic extracts were washed with water and extracted with tartaric acid solution (10%). The extract was washed (dichloromethane), basified with 2M sodium hydroxide solution and further extracted with methylene chloride. The extracts were washed (water), dried and evaporated to give an oily product.
(4) The residue was purified by column chromatography on silica eluting with methanol/dichloromethane (1:9).
(5) The residue was dissolved in dichloromethane and extracted with 1M hydrochloric acid. The combined acidic extracts were washed (dichloromethane) and basified with 2M sodium hydroxide solution. The basic solution was extracted with ethyl acetate and the combined organic extracts washed (water), dried and evaporated to give an oily product.

Ex 56: 4-[3-(Imidazol-1-yl)propyl]-1-(3-phenylpropionyl)piperidine
Ex 57: 1-[3-(4-Chlorophenyl)propionyl]-4-[2-(2-methylimidazol-1-yl)ethyl]piperidine

EXAMPLES 58–66

Compounds of formula X were also prepared in a similar manner to that described in Example 51 by reacting a compound of formula XV with compounds of formula XVI as shown in Table 7 below. In each of these Examples 0.7 g sodium hydride was used in the reaction, except where shown.

The compounds of formula XV are known in the art: Y is group III (a), in which $R_9$ is hydrogen, and $R_1$, $R_2$ and $R_3$ are hydrogen, X is a bond, $alk^1$ is $(CH_2)_2$, j and b are 1, k is 0, Hal is chloro and $alk^2$ is defined in Table 7 below.

Compounds of formula XVI are known in the art: Z is defined in Table 7 in terms of groups V(a)–(h) (with substituents $R_{11}$–$R_{14}$) as hereinabove defined.

TABLE 7

|         | Compound XV |         | Compound XVI |          |          |          |          |          | Reaction Time | Cpd. X    |       |
|---------|-------------|---------|--------------|----------|----------|----------|----------|----------|---------------|-----------|-------|
| Example | $alk^2$     | Amt (g) | Gp Z         | $R_{11}$ | $R_{12}$ | $R_{13}$ | $R_{14}$ | Amt (g)  | (hrs)         | m. pt. °C.| Notes |
| 58 | $(CH_2)_2$ | 2.5 | Va | H        | H        | $i-C_3H_7$  | — | 1.0 | 5.0 | Oil | 2    |
| 59 | $(CH_2)_2$ | 2.5 | Va | H        | H        | $C_2H_5$    | — | 0.9 | 5.0 | Oil | 2    |
| 60 | $(CH_2)_2$ | 2.5 | Va | $C_6H_5$ | $C_6H_5$ | H           | — | 2.0 | 5.0 | Oil | 2    |
| 61 | $(CH_2)_2$ | 2.5 | Va | H        | H        | $C_6H_5$    | — | 1.3 | 5.0 | Oil | 2    |
| 62 | $(CH_2)_2$ | 2.5 | Va | H        | H        | $C_{11}H_{23}$ | — | 2.0 | 5.0 | Oil | 2    |
| 63 | $(CH_2)_2$ | 2.5 | Va | H        | H        | $n-C_3H_7$  | — | 1.0 | 2.5 | Oil |      |
| 64 | $(CH_2)_2$ | 2.5 | Vb | H        | H        | —           | — | 0.6 | 4.0 | Oil |      |
| 65 | $(CH_2)_2$ | 2.5 | Vh | $CH_3$   | —        | —           | H | 1.2 | 4.2 | Oil | 1    |
| 66 | $CH_2$     | 2.0 | Va | H        | H        | $C_2H_5$    | — | 0.7 | 3.9 | Oil | 3, 4 |

Notes (1) The product was purified by flash chromatography by eluting with dichloromethane/methanol (9:1).

(2) The residue was purified by column chromatography eluting with 4–6% methanol/dichloromethane (1:9) on silica.

(3) The organic extracts were washed with water and extracted with tartaric acid solution (10%), then washed (dichloromethane) and basified with 2M sodium hydroxide solution. Extraction with dichloromethane, washing (water, drying and evaporating gave an oily product.

(4) 0.5 g sodium hydride used in reaction.

The compounds prepared in Examples 58–66 were as follows:

Ex 58: 4-[2-(2-Isopropylimidazol-1-yl)ethyl]-1-(3-phenylpropionyl)piperidine
Ex 59: 4-[2-(2-Ethylimidazol-1-yl)ethyl]-1-(3-phenylpropionyl)piperidine
Ex 60: 4-[2-(4,5-Diphenylimidazol-1-yl)ethyl]-1-(3-phenylpropionyl)piperidine
Ex 61: 4-[2-(2-Phenylimidazol-1-yl)ethyl]-1-(3-phenylpropionyl)piperidine
Ex 62: 1-(3-Phenylpropionyl)-4-[2-(2-undecylimidazol-1-yl)ethyl]piperidine
Ex 63: 1-(3-Phenylpropionyl)-4-[2-(2-propylimidazol-1-yl)ethyl]piperidine
Ex 64: 1-(3-Phenylpropionyl)-4-[2-(1H-1,2,4-triazol-1-yl)ethyl]piperidine
Ex 65: 2-Methyl-1-{2-[1-(3-phenylpropionyl)piperidin-4-yl]ethyl)benzimidazole
Ex 66: 4-(2-Ethylimidazol-1-ylmethyl-1-(3-phenylpropionyl)piperidine

EXAMPLE 67

4-[2-(2-Methylimidazol-1-yl)ethyl]-1-(3-phenylpropionyl)piperidine was prepared as an oily product in a similar manner to that described in Example 51 above by reacting a compound of formula XV as prepared in Example 42 (10.0 g) with 2-methylimidazole (3.0 g).

EXAMPLE 68

(a) A solution of 3-phenylpropionyl chloride (6.3 ml) in dry dichloromethane (11 ml) was added dropwise to a cooled solution of the product from Example 21 (5.3 g) and triethylamine (7.1 ml) in dichloromethane (55 ml), whilst maintaining the temperature at 0° C. The reaction mixture was stirred at 0° C. for 1–2 hours, then allowed to warm to 20° C. with stirring for 22 hours.

(b) Following filtration, the filtrate was washed (5M sodium hydroxide solution, water) and then extracted with tartaric acid (10%). The combined aqueous extracts were basified (5M sodium hydroxide solution), extracted with dichloromethane, and the extracts dried and concentrated to give 4-[2-(imidazol-1-yl)-methylethyl]-1-(3-phenylpropionyl)piperidine.

EXAMPLES 69–85

In a similar manner to that described in Example 68 (a) above, compounds of formula X were prepared by reacting compounds of formula VIII and compounds of formula IX as shown in Table 8 below.

When compounds of formula VIII are known in the art, $R_2$ and $alk^1$ are as defined in Table 8 below and $R_1$ and $R_3$ are hydrogen, X is a bond, b is 1 and Hal is chloro. When compounds of formula VIII are novel intermediates their preparative Example is described Table 8 below. In the 'Amount' column, '(all)' indicates that the entire product of the preparative Example is used in the reaction.

When compounds of formula IX are known in the art, they are represented in Table 8 by the designation IX. Compound IX(I) is a compound in which Y is a group of formula IIIa as hereinabove defined, $R_9$ is hydrogen, $alk^2$ is $CH_2CH_2$, Z is a group of formula Va as hereinabove defined, $R_{11}$, $R_{12}$ and $R_{13}$ are hydrogen and k is 0. When compounds of formula IX are novel intermediates, their preparative Example is defined in Table 8 below

TABLE 8

| | Compound VIII | | | Compound IX | | Et₃N | Reaction Time at | Cpd X | |
|---|---|---|---|---|---|---|---|---|---|
| Ex | R₂ | alk¹ | Amt (ml) | Structure | Amt (g) | Amt (ml) | 20° C. (hrs) | m. pt °C. | Notes |
| 69 | H | (CH₂)₂ | 0.7 | Preparative Example 22 | 1.0 | 0.7 | 16 | Oil | 1 |
| 70 | H | (CH₂)₂ | 1.0 | Preparative Example 23 | 1.4 | 1.1 | 16 | Oil | 2a |
| 71 | H | (CH₂)₂ | 2.2 | Preparative Example 24 | 2.2 | 2.5 | 16 | Oil | 3 |
| 72 | H | (CH₂)₂ | 2.8 | Preparative Example 25 | 2.8 | 3.1 | 21 | Oil | 3 |
| 73 | H | (CH₂)₂ | 2.6 | Preparative Example 26 | 2.7 | 3.0 | 22 | Oil | 3 |
| 74 | H | (CH₂)₂ | 1.0 | Preparative Example 27 | 1.1 | 1.0 | 64 | Oil | 1 |
| 75 | H | (CH₂)₂ | 1.0 | Preparative Example 28 | 1.2 | 1.0 | 16 | Oil | 1 |
| 76 | H | (CH₂)₂ | 1.3 | Preparative Example 29 | 1.2 | 1.3 | 80 | Oil | 1, 2b |
| 77 | Preparative Example 3 | | 1.6 g | IX(I) | 1.5 | 0.9 g | 20 | Oil | 1 |
| 78 | Preparative Example 4 | | (all) | IX(I) | 1.8 | 1.5 | 32 | Oil | 1 |
| 79 | Preparative Example 5 | | 1.8 | IX(I) | 1.5 | 0.9 g | 20 | Oil | 1 |
| 80 | Preparative Example 6 | | 1.1 | IX(I) | 1.0 | 0.6 | 20 | Oil | 1 |
| 81 | Preparative Example 7 | | (all) | IX(I) | 1.5 | 2.0 | 100 | Oil | 1, 3 |
| 82 | Preparative Example 9 | | (all) | IX(I) | 0.9 | 0.6 | 16 | Oil | 3 |

TABLE 8-continued

| | Compound VIII | | | Compound IX | | Et₃N | Reaction Time at | Cpd X | |
|----|----|----|----|----|----|----|----|----|----|
| Ex | R₂ | alk¹ | Amt (ml) | Structure | Amt (g) | Amt (ml) | 20° C. (hrs) | m. pt °C. | Notes |
| 83 | Preparative Example 8 | | (all) | Prep. Example 30 | 1.5 | 0.9 g | 16 | Oil | 1 |
| 84 | H | CH₂ | 2.3 | IX(I) | 1.8 | 2.3 | 44 | Oil | 1, 4 |
| 85 | Preparative Example 9 | | (all) | IX(I) | 1.8 | 1.5 | 20 | Oil | 1 |

Notes (1) The resulting solution was diluted with dichloromethane, washed (2M sodium bicarbonate solution, water), dried and evaporated to give a gum.

(2) The product was purified by flash chromatography eluting with (a) methanol/ethyl acetate (9:1) or (b) ethyl acetate/triethylamine (9:1).

(3 Purification as described in Example 68(b).

(4 Reaction mixture stirred at 0°–5° C.

(5 The resulting solution was diluted with dichloromethane, washed (2M sodium bicarbonate solution, water); the dichloromethane solution was extracted with 1M hydrochloric acid and the extracts basified with 1M sodium hydroxide solution and then further extracted with ethyl acetate. The ethyl acetate extracts were washed (brine), dried and evaporated to give an oily residue.

The compounds prepared in Table 8 were as follows:

Ex 69: 1-{2-[1-(3-Phenylpropionyl)piperidin-4-yl] ethyl}benzimidazole

Ex 70: 4-[2-(4,5-Dichloro-2-methylimidazol-1-yl)ethyl]-1-(3-phenylpropionyl)piperidine Ex 71: 4-[2-(4,5-Dimethylimidazol-1-yl)ethyl]-1-(3-phenylpropionyl)piperidine Ex 72: 4-[2-(2-Methylimidazol-1-yl)ethyl]-1-(3-phenylpropionyl)piperidine Ex 73: 4-[2-(4-Methylimidazol-1-yl)ethyl]-1-(3-phenylpropionyl)piperidine and 4-[2-(5-Methylimidazol-1-yl)ethyl]-1-(3-phenylpropionyl)piperidine Ex 74: 4-[2-(1H-1,2,3-Triazol-1-yl)ethyl]-1-(3-phenylpropionyl)piperidine Ex 75: 4-[2-(2H-1,2,3-Triazol-2-yl)ethyl]-1-3-phenylpropionyl)piperidine Ex 76: 1-(3-Phenylpropionyl)-4-[2-(2H-tetrazol-2-yl)ethyl] piperidine Ex 77: 4-[2-(Imidazol-1-yl)ethyl]-1-[3-(4-methylphenyl) propionyl]piperidine Ex 78: 1-[3-(4-Chlorophenyl)propionyl]-4-[2-(imidazol-1-yl)ethyl]piperidine Ex 79: 4-[2-(Imidazol-1-yl)ethyl]-1-[3-(4-methoxyphenyl) propionyl]piperidine Ex 80: 4-[2-(Imidazol-1-yl)ethyl]-1-(1,2,3,4-tetrahydro-2-naphthoyl)piperidine Ex 81: 4-[2-(Imidazol-1-yl)ethyl]-1-(3-phenylbutyroyl) piperidine Ex 82: 4-[2-(2-Methylimidazol-1-yl) ethyl]-1-(4-phenylbutyroyl)piperidine Ex 83: 4-[2-(Imidazol-1-yl)ethyl]-1-[3-(4-methylthiophenyl)propionyl]piperidine Ex 84: 4-[2-(Imidazol-1-yl)ethyl]-1-phenylacetylpiperidine Ex 85: 4-[2-(Imidazol-1-yl)ethyl]-1-(4-phenylbutyroyl) piperidine

EXAMPLE 86

(a) A mixture of 4-[2-(imidazol-1-yl)ethyl]piperidine (1.5 g), triethylamine (4.7 ml), 2-bromoethyl phenyl sulphide (3.6 g), dry ethanol (10 ml) and dry toluene (20 ml) was heated under reflux at 80°–100° C. for 40 hours.

(b) The reaction solution was evaporated and the resulting residue partitioned between 2M hydrochloric acid and ethyl acetate. The aqueous layer was separated off, washed (ethyl acetate), basified (5M sodium hydroxide solution), extracted with dichloromethane and the extracts were dried and evaporated to give 4-[2-(imidazol-1-yl)ethyl]-1-(2-phenylthioethyl)piperidine as an oil.

EXAMPLES 87–92

In a similar manner to that described in Example 86 (a) above, compounds of formula I were prepared by reacting compounds of formula VIII and compounds of formula IX as described in Table 9 below.

Compounds of formula VIII are known compounds with X, R₂, alk¹ and Hal defined as in Table 9 below, and R₁ and R₃ are hydrogen and b is 0.

When compounds of formula IX are novel intermediates, their preparative Example is given in Table 9 below. The known compound of formula IX is represented in Table 9 by IX(I) with Y being a group of formula IIIa as hereinabove defined, R₉ is hydrogen, alk² is CH₂CH₂, Z is a group of formula Va as hereinabove defined R₁₁, R₁₂ and R₁₃ are hydrogen and k is 0.

TABLE 9

| | Compound VIII | | | | Compound IX | | Reaction | Compound I | |
|----|----|----|----|----|----|----|----|----|----|
| Ex | X | R₂ | alk¹ | Hal | Amt (ml) | Structure | Amt (g) | Time (hrs) | m.p. °C. | Notes |
| 87 | O | H | (CH₂)₂ | Br | 4.1 | IX(I) | 3.0 | 22 | Oil | 1, 6 |
| 88 | CO | H | (CH₂)₃ | Cl | 3.4 g | IX(I) | 1.5 | 32 | 79–81 | 1, 5a |
| 89 | CO | H | (CH₂)₂ | Cl | 4.1 g | IX(I) | 2.0 | 32 | 67–70 | 1, 2a |
| 90 | HC=CH | H | CH₂ | Br | 3.3 | IX(I) | 1.5 | 32 | Oil | 1, 2b |
| 91 | NHCO | 4-CF₃ | CH₂ | Cl | 2.0 g | IX(I) | 1.5 | 22 | Oil | 4, 5b |
| 92 | — | H | (CH₂)₃ | Br | 1.0 g | Prep Ex 31 | 1.0 | 32 | Oil | 1, 2a |

Notes
(1) Purification as described in Example 86(b).
(2) Purification by column chromatography eluting with
(a) dichloromethane/methanol (9:1);
(b) dichloromethane/methanol (1:1) on silica gel gave solid product.
(4) The resulting solution was evaporated, the residue partitioned between ethyl acetate and water, extracted with ethyl acetate and the extracts were dried.
(5) Purification by flash chromatography eluting with
(a) dichloromethane/methanol (2:1);
(b) dichloromethane/methanol (9:1).
(6) Further purification by distillation.

The compounds prepared in Table 8 above were as follows:

Ex 87: 4-[2-(Imidazol-1-yl)ethyl]-1-(2-phenoxyethyl) piperidine
Ex 88: 4-[2-(Imidazol-1-yl)ethyl]-1-(4-oxo-4-phenylbutyl) piperidine
Ex 89: 4-[2-(Imidazol-1-yl)ethyl]-1-(3-oxo-3-phenylpropyl) piperidine
Ex 90: 1-Cinnamyl-4-[2-(imidazol-1-yl)ethyl]-piperidine
Ex 91: 4-[2-(Imidazol-1-yl)ethyl]piperidino-4'-trifluoromethylacetanilide
Ex 92: 4-{2-[-(2-(2-Chlorobenzoyl)imidazol-1-yl]-ethyl}-1-(3-phenylpropyl)piperidine

EXAMPLE 93

A mixture of the product from Example 20 (3.6 g), triethylamine (2.8 ml), N,N-dimethylformamide (40 ml) and 4-chloro-α-methylbenzyl chloride (3.5 g) was heated at 80°–100° C. for 16 hours. The mixture was cooled and poured into water and then was extracted with dichloromethane. The combined dichloromethane extracts were back extracted with 2M hydrochloric acid. The combined acidic layers were washed with dichloromethane, basified with 2M sodium hydroxide solution and extracted with dichloromethane. The combined organic layers were washed (water), dried, filtered and evaporated to give an oil. The oil was dissolved in ether, filtered and the filtrate was acidified with a solution of hydrogen chloride in ether to give a solid which was collected by filtration and recrystallised from absolute ethanol/ether. The solid was partitioned between saturated sodium bicarbonate solution and dichloromethane and the organic phase was dried, filtered and evaporated to give an oil which was flash-chromatographed on Sorbsil® using ethyl acetate/methanol/triethylamine (18:2:1) to give a waxy solid. Trituration with petroleum ether (b.p. 60°–80° C.) gave 1-[1-(4-chlorophenyl)ethyl]-4-[2-(imidazol-1-yl-ethyl]piperidine, m.p. 79°–80° C.

EXAMPLE 94

A solution of oxalyl chloride (5 ml) was added to a solution of 3-(4-methylphenyl)propionic acid (0.9 g) dichloromethane (20 ml) which contained N,N-dimethylformamide (0.3 ml). The mixture was stirred at 20° C. for 16 hours. On evaporation, the resulting oil was dissolved in dichloromethane (5 ml) and then added to a stirred solution of the product from Example 30 (0.9 g) in dichloromethane (10 ml) which contained triethylamine (0.5 g). The reaction mixture was stirred at 20° C. for 16 hours. After dilution with dichloromethane the reaction mixture was washed (saturated sodium bicarbonate solution) and extracted with 1M hydrochloric acid. The combined acidic extracts were basified with 2M sodium hydroxide solution and extracted with ethyl acetate and the combined extracts washed (brine), dried and evaporated to give 4-[2-(2-methylimidazol-1-yl)ethyl]-1[3-(4-methylphenyl) propionyl]piperidine as an oil.

EXAMPLE 95

(a) A solution of 1-chloro-3-phenylpropane (5.4 g) in toluene (10 ml) was added to a stirred solution of piperazine (15.0 g) and triethylamine (3.5 g) in toluene (20 ml) at 100° C. The reaction mixture was heated with stirring at 100° C. for 0.2 hours and then heated under reflux for 18 hours. The reaction mixture was allowed to cool to room temperature and then filtered. The filtrate was evaporated and the residual oil was purified by column chromatography, eluting with dichloromethane/methanol (19:1), then methanol, to give 1-(3-phenylpropyl)piperazine as an oil.

(b) A solution of 1-(2-hydroxyethyl)imidazole (3.0 g) in toluene (50 ml) was treated with thionyl chloride (9.0 g) and the mixture was heated with stirring at 100° C. for 2 hours. Excess thionyl chloride and toluene were then removed by evaporation and the residue basified (saturated sodium carbonate solution) and extracted with dichloromethane. The combined organic extracts were washed (water), dried and evaporated to give 1-(2-chloroethyl)imidazole as an oil.

(c) A mixture of the product from part (a) above (2.8 g), the product from part (b) above (2.0 g), sodium bicarbonate (2.1 g) and industrial methylated spirits (110 ml) was heated under reflux with stirring for 32 hours. The reaction mixture was evaporated and water (100 ml) then added. The suspension was extracted with dichloromethane and the combined extracts dried and evaporated to give 1-[2-(imidazol-1-yl)ethyl]-4-(3-phenylpropyl)piperazine as an oil. The oil was purified by column chromatography eluting with dichloromethane/methanol (1:1) on silica gel to give an oily product which was then dissolved in hot ethanol and cooled. Ethereal hydrogen chloride was added and the resulting gum triturated and then filtered to give 1-[2-imidazol-1-yl)ethyl]-4-(3-phenylpropyl)piperazine trihydrochloride, m.p. 245°–247° C.

EXAMPLE 96

Sodium bicarbonate (2.9 g) was added to a solution of 1-(2-chloroethyl)imidazole (4.0 g) and 4-(3-phenylpropyl) piperidine (6.2 g) in industrial methylated spirits (100 ml) and the reaction mixture heated under reflux for 96 hours. The reaction mixture was then filtered and the filtrate concentrated to give an oil, which was purified by flash chromatography eluting with ethylacetate/methanol/triethylamine (88:10:2). The solid obtained was dissolved in ether, ethereal hydrogen chloride acid was added and the solid precipitated was collected and recrystallised from ethanol/ether to give 1-[2-(imidazol-1-yl)ethyl]-4-(3-phenylpropyl)piperidine, dihydrochloride monohydrate, m.p. 178°–179° C.

EXAMPLE 97

A mixture of 4-(3-phenylpropyl)piperidine (6.2 g), 1-(2-chloroethyl)triazole (6.0 g), sodium bicarbonate (2.9 g) and industrial methylated spirits (100 ml) were heated under reflux with stirring under nitrogen for 40 hours. The mixture was then evaporated and the resulting oil purified by flash chromatography, eluting with triethylamine/acetonitrile (1:49) gave an oily product. Treatment with ethereal hydrogen chloride and recrystallisation of the solid from ethanol/ether gave 1-[2-(1H-1,2,4-triazol-1-yl)ethyl]-4-(3-phenylpropyl)piperidine dihydrochloride, m.p. 185°–187° C.

EXAMPLE 98

(a) A solution of borane/tetrahydrofuran (53 ml, 1M solution in tetrahydrofuran) was added dropwise with stirring to a solution of the product from Example 50 (3.3 g) in dry tetrahydrofuran (50 ml) under nitrogen. The mixture was stirred for 16 hours at 20° C. then the solvent was removed under reduced pressure. The residue was heated to 80°–100° C. under nitrogen for 1 hour. 1M Hydrochloric acid (40 ml) was added and the mixture heated to 80°–100° C. for a further 2 hours. The mixture was cooled and basified with 5M sodium hydroxide solution. The mixture was extracted with ethyl acetate and the combined organic extracts were dried, filtered and evaporated to give an oil.

(b) The oil from part (a) was dissolved in ether and decanted from some insoluble material. The solution was treated with an excess of a solution of hydrogen chloride in ether and the material which separated was filtered off to give a solid which was recrystallised from ethanol/ether to give 4-[2-(imidazol-1-yl)ethyl]-1-(3-phenylpropyl) piperidine dihydrochloride, m.p. 173°–174° C.

EXAMPLES 99–129

In a similar manner to that described in Example 98(a), compounds of formula I were prepared by reducing compounds of formula X as shown in Table 10 below.

The preparative Example of each of compounds 99°–129 is given in Table 10 below. In each of the Examples below, the time of heating the residue after the removal of the solvent was 1 hour and the time of heating after addition of hydrochloric acid was 2 hours. The reaction time for the initial stirring at 20° C. is given in Table 10 below.

Where 'all' is stated in the 'Amount' column, the entire product of the preparative Example was used.

TABLE 10

| | Compound X | | | | |
|---|---|---|---|---|---|
| Example | Preparative Example | Amount (g) | Reaction Time (hours) | Compound I m. pt (°C.) | Notes |
| 99 | 51 | 0.7 | 16 | Oil | |
| 100 | 52 | 2.0 | 16 | Amorphous solid | 1 |
| 101 | 53 | 3.3 | 22 | Oil | |
| 102 | 54 | 1.7 | 16 | Oil | |
| 103 | 55 | 1.5 | 16 | Oil | |
| 104 | 56 | 0.6 | 16 | Oil | |
| 105 | 57 | 0.7 | 72 | Oil | |
| 106 | 58 | 1.4 | 64 | Oil | 2 |
| 107 | 59 | 1.3 | 16 | Oil | |
| 108 | 60 | 2.9 | 16 | Oil | 3 |
| 109 | 61 | 2.3 | 16 | Oil | |
| 110 | 63 | 1.4 | — | Oil | 4 |
| 111 | 64 | 2.9 | — | Oil | 4, 5 |
| 112 | 65 | 0.5 | 16 | Oil | 5 |
| 113 | 68 | 2.5 | 16 | Oil | |
| 114 | 69 | 1.2 | 16 | Oil | 6 |
| 115 | 70 | 1.3 | 16 | Oil | |
| 116 | 71 | 2.0 | 16 | Oil | |
| 117 | 72 | 1.0 | 16 | Oil | |
| 118 | 73 | 3.4 | 16 | Oil | 7 |
| 119 | 74 | 0.5 | — | 64–6 | 4 |
| 120 | 75 | 0.5 | 16 | Oil | 5 |
| 121 | 76 | 0.8 | — | Oil | 4, 5 |
| 122 | 77 | 0.5 | 16 | Oil | |
| 123 | 78 | 1.0 | 16 | Oil | |
| 124 | 79 | 2.5 | 16 | Oil | |
| 125 | 80 | 1.6 | 16 | 42–46 | |
| 126 | 81 | 1.5 | 16 | Oil | |
| 127 | 83 | 2.4 | 16 | Oil | 2 |
| 128 | 84 | (all) | 23 | Oil | |
| 129 | 85 | (all) | 22 | Oil | |

Notes:

(1) The oil produced was dissolved in the minimum volume of ethanol and treated with a solution of tartaric acid (0.07 g) in ethanol (1 ml), then diluted with ether. The solid obtained was collected by filtration.

(2) After extraction with ethyl acetate, the residue was further extracted with 10% aqueous tartaric acid solution and then basified (2M sodium hydroxide solution). Extraction with ethyl acetate and washing (brine), drying and evaporation gave an oily product.

(3) The oil produced was purified by column chromatography eluting with methanol/dichloromethane (1:9) on silica gel.

(4) Lithium aluminium hydride (2.5 equivalents) was used in replacement for the borane/tetrahydrofuran complex except for Example 121 where 3.3 equivalents were used. The reaction mixture was cooled, then stirred at 20° C. for 2–5 hours, cooled to 0°–5° C. and treated with water followed by 2M hydrochloric acid.

(5) The resulting oil was purified by flash chromatography eluting with dichloromethane/methanol (1:1) on Sorbsil®.

(6) The resulting oil was purified by preparative layer chromatography developing with ethyl acetate/triethylamine (9:1).

(7) A mixture of isomers was obtained.

Table 11 lists all the compounds of formula I prepared in Examples 99–129:

TABLE 11

Ex 99: 3-[2-(Imidazol-1-yl)ethyl]-1-(3-phenylpropyl) piperidine

Ex 100: 2-[2-(Imidazol-1-yl)ethyl]-1-(3-phenylpropyl) piperidine

Ex 101: 3-Imidazol-1-ylmethyl-1-(3-phenylpropyl) piperidine

Ex 102: 4-Imidazol-1-ylmethyl-1-(3-phenylpropyl) piperidine

Ex 103: 4-[2-(Imidazol-1-yl)ethyl]-3-methyl-1-(3-phenylpropyl)piperidine

Ex 104: 4-[3-(Imidazol-1-yl)propyl]-1-(3-phenylpropyl) piperidine

Ex 105: 1-[3-(4-Chlorophenyl)propyl]-4-[2-(2-methylimidazol-1-yl)ethyl]piperidine Ex 106: 4-[2-(2-Isopropylimidazol-1-yl)ethyl]-1-(3-phenylpropyl)piperidine Ex 107: 4-[2-(2-Ethylimidazol-1-yl)ethyl]-1-(3-phenylpropyl)piperidine Ex 108: 4-[2-(4,5-Diphenylimidazol-1-yl)ethyl]-1-(3-phenylpropyl)piperidine Ex 109: 4-[2-(2-Phenylimidazol-1-yl)ethyl]-1-(3-phenylpropyl)piperidine Ex 110: 1-(3-Phenylpropyl)-4-[2-(2-propylimidazol-1-yl) ethyl]piperidine Ex 111: 1-(3-Phenylpropyl)-4-[2-(1H-1,2,4-triazol-1-yl)ethyl]piperidine Ex 112: 2-Methyl-1-{2-[1-(3-phenylpropyl)piperidin-4-yl] ethyl}benzimidazole
Ex 113: 4-[2-(Imidazol-1-yl)-1-methylethyl]-1-(3-phenylpropyl)piperidine
Ex 114: 1-{2-[1-(3-Phenylpropyl)piperidin-4-yl]-ethyl}benzimidazole
Ex 115: 4-[2-(4,5-Dichloro-2-methylimidazol-1-yl)ethyl]-1-(3-phenylpropyl)piperidine
Ex 116: 4-[2-(4,5-Dimethylimidazol-1-yl)ethyl]-1-(3-phenylpropyl)piperidine
Ex 117: 4-[2-(2-Methylimidazol-1-yl)ethyl]-1-(3-phenylpropyl)piperidine
Ex 118: 4-[2-(4-Methylimidazol-1-yl)ethyl]-1-(3-phenylpropyl)piperidine and 4-[2-(5-Methylimidazol-1-yl)ethyl]-1-(3-phenylpropyl)piperidine
Ex 119: 1-(3-Phenylpropyl)-4-[2-(1$\underline{H}$-1,2,3-triazol-1-yl)ethyl]piperidine
Ex 120: 1-(3-Phenylpropyl)-4-[2-(2$\underline{H}$-1,2,3-triazol-2-yl)ethyl]piperidine
Ex 121: 1-(3-Phenylpropyl)-4-[2-(2$\underline{H}$-tetrazol -2-yl)ethyl] piperidine
Ex 122: 4-[2-(Imidazol-1-yl)ethyl]-1-[3-(4-methylphenyl)propyl]piperidine
Ex 123: 1-[3-(4-Chlorophenyl)propyl]-4-[2-(imidazol-1-yl)ethyl]piperidine
Ex 124: 4-[2-(Imidazol-1-yl)ethyl]-1-[3-(4-methoxyphenyl)propyl]piperidine
Ex 125: 4-[2-(Imidazol-1-yl)ethyl]-1-(1,2,3,4-tetrahydronaphth-2-ylmethyl)piperidine
Ex 126: 4-[2-(Imidazol-1-yl)ethyl]-1-(3-phenylbutyl) piperidine
Ex 127: 4-[2-(Imidazol-1-yl)ethyl]-1-[3-(4-methylthiophenyl)propyl]piperidine
Ex 128: 4-[2-(Imidazol-1-yl)ethyl]-1-phenethylpiperidine
Ex 129: 4-[2-(Imidazol-1-yl)ethyl]-1-(4-phenylbutyl) piperidine

EXAMPLE 130

In the preparation of capsules, 10 parts by weight of active compound and 240 parts by weight of lactose are de-aggregated and blended. The mixture is filled into hard gelatin capsules, each capsule containing 10 mg active compound.

EXAMPLE 131

In the preparation of capsules, 50 parts by weight of active compound, 300 parts by weight of lactose and 3 parts by weight of magnesium stearate are de-aggregated and blended. The mixture is filled into hard gelatin capsules, each capsule containing 50 mg of active ingredient.

EXAMPLE 132

Tablets are prepared from the following ingredients.

|                     | Parts by weight |
|---------------------|-----------------|
| Active compound     | 10              |
| Lactose             | 190             |
| Maize starch        | 22              |
| Polyvinylpyrrolidone| 10              |
| Magnesium stearate  | 3               |

The active compound, the lactose and some of the starch are de-aggregated, blended and the resulting mixture is granulated with a solution of the polyvinylpyrrolidone in ethanol. The dry granulate is blended with magnesium stearate and the rest of the starch. The mixture is then compressed in a tableting machine to give tablets containing:

a) 10 mg
b) 100 mg
c) 500 mg of active compound.

EXAMPLE 133

Tablets are prepared by the method of Example 132. The tablets are enteric coated in a conventional manner using a solution of 20% cellulose acetate phthalate and 3% diethyl phthalate in ethanol:dichloromethane (1:1).

EXAMPLE 134

In the preparation of suppositories, 100 parts by weight of active compound is incorporated in 1300 parts by weight of semi-synthetic glycerides as the suppository base and the mixture formed into suppositories each containing 100 mg of active ingredient.

EXAMPLE 135

In the preparation of ointments the active compound is incorporated into the base by thorough homogenization until the drug is evenly distributed. The ointment is packed into 10 g amber jars with screw-capped lined lids.

Active compound 0.1g
White soft paraffin to 10 g

The therapeutic activity of the compounds of the present invention has been demonstrated by activity in one or both of the tests A and B below. Activity in at least one of these tests indicates immumodulatory activity. Further information about therapeutic activity was also provided by activity in any one of tests C, D and E below.

The therapeutic activity of preferred compounds of the present invention has been demonstrated by an in vitro mixed lymphocyte reaction (Test A) which is an in vitro correlate of in vivo cellular immune reactivity. A mixed lymphocyte reaction (MLR) occurs when lymphocytes from two genetically dissimilar individuals, or inbred strains of mice are cultured together. An MLR results in the activation and proliferation of lymphocytes, which is measured by the incorporation of radiolabelled thymidine into the cellular DNA synthesised during cell division. A 'one-way' MLR is used to determine the immunosuppressive activity of test compounds in vitro. In this reaction one population of spleen cells serves as the stimulator cells and is treated with mitomycin C to prevent cell division. Spleen cells from a second allogeneic population (responder cells) are untreated and when mixed with the stimulator cells are able to undergo division which is measured. The degree of proliferation is measured in the presence and absence of test compound to assess the immunosuppressive activity of the compound.

The techniques for carrying out lymphocyte proliferation assays including MLRs are well known, eg Bradley, pages 156–166, in Mishell and Shiigi, Eds. Selected Methods in Cellular immunology (Freeman, San Francisco, 1980); and Battisto et al, methods in Enzymology 1987; 150: 83–91. Various slight modifications of these techniques are in use and that used herein is described in Gibb, Webber and Bowen, J immunological Methods 1985; 81: 107–113.

Test A was carried out in the following manner:
Mixed Lymphocyte Reaction (Test A)

Cell suspensions obtained from the spleens of female BALB/c and $C_{57}BL/6$ strain mice of between 6 and 9 weeks of age were used as sources of responder and stimulator cells respectively. The mice were killed using a rising concentration of $CO_2$ and the spleens removed aseptically and teased using a scalpel and forceps to produce a single cell suspension in Hanks balanced salt solution (HBSS). The suspensions were filtered through cell strainers (Falcon), sedimented by centrifugation and resuspended in Tris-buffered ammonium chloride pH 7.2 (medium D) to lyse the erythrocytes. The cells were sedimented again and washed twice in HBSS before resuspending in complete RPMI 1640 tissue culture medium (medium E). The $C_{57}BL/6$ cells were resuspended to 9 mls per spleen and a solution of mitomycin C at 400 µg/ml in medium E added to give a final concentration of 40 µg/ml. After incubation of the $C_{57}BL/6$ cells at 37° C. for 30 minutes in an atmosphere of 5% $CO_2$ and 95% air, the cells were sedimented and washed 3 times in medium E. Both cell suspensions were diluted in medium E to $5 \times 10^6$ cells/ml. 100 µl of each of the responder and stimulator cell suspensions were aliquoted into the wells of 96 well flat bottom microtitre plates containing 50 µl of test compound at an appropriate dilution (initially 50 µM diluted in medium E from a stock solution at 100 mM in dimethyl sulphoxide) giving a final test compound concentration of 10 µM (final dilution). Compounds active at this concentration were tested at further final dilution of 1 µM, 0.1 µM and 0.01 µM and 0.001 µM to determine the concentration of test compound which causes 50% inhibition of the immune response ($IC_{50}$). After four days of culture at 37° C. in a humidified atmosphere of 5% $CO_2$ and 95% air, 1 µCi of tritiated thymidine in 20 µl of medium E was added to each well and the plates incubated for a further 24 hours. Cells were then harvested onto Inotech G7 glass fibre filter mats using an Inotech cell harvester. The filters were transferred to vials to which 2 ml of Packard Emulsifier-Safe scintillation fluid was added and the radioactivity from the incorporated thymidine was counted in a Packard liquid scintillation counter. The counts per minute (CPM) reflect the degree of lymphocyte proliferation. The data were analysed to determine the percentage inhibition of lymphocyte proliferation by the test compound. Compounds were deemed active if they reproducibly inhibited proliferation by $\geq 50\%$ in the absence of toxicity at a concentration of $\leq 10$ µM in at least two out of three tests.

Medium D (for erythrocyte lysis)
Stock solutions 0.17M Tris. Tris base (20.6 g) was dissolved in distilled water (900 ml) and the pH adjusted to 7.65 with dilute hydrochloric acid. The volume was made up to 1000 ml with distilled water.

0.16M Ammonium chloride: Ammonium chloride (8.3 g) was dissolved in distilled water (1000 ml).

Working solutions

The Tris stock solution (10 ml) and ammonium chloride stock solution (90 ml) were mixed, the pH adjusted to 7.2 with dilute hydrochloric acid and the solution filter sterilised.

Medium E (for cell culture)

RPMI 1640 tissue culture medium containing 2.0 gl sodium bicarbonate (ICN FLOW) supplemented with 5–10% serum supplement (foetal calf serum, Sigma or Nu-Serum, Collaborative Biomedical Products) 2 mM L-glutamine (ICN Flow), 50 IU/ml penicillin (ICN Flow), 50 µg/ml streptomycin (ICN FLOW) and $5 \times 10^{-5}$M 2-mercaptoethanol Sigma).

MLR data were expressed as the percentage inhibition of lymphocyte proliferation caused by the test compound, calculated by the formula $$\% \text{ inhibition} = 100 - \frac{\text{test} \times 100}{\text{control}}$$

where:
control=CPM thymidine incorporation by responder cells mixed with stimulator cells in the absence of compound
test=CPM thymidine incorporation by responder cells mixed with stimulator cells in the presence of test compound.

As stated above, a compound was deemed active if it reproducibly inhibited proliferation by $\geq 250\%$ in the absence of toxicity at a concentration of $\leq 10$ µM in at least two out of three tests.

The mean inhibitory effect of compounds at each concentration was plotted as ordinate values on a graph against the concentration of compound on the abscissa in a logarithmic (10) scale. Linear interpolation was then used to determine the concentration of compound which caused a 50% inhibition of the proliferative response ($IC_{50}$).

Table A below lists compounds of formula I deemed to be active in Test A. The concentration of test compound which is calculated to cause a 50% inhibition of the immune response (IC 50) for each compound is given in Table A. The symbol $\leq$ indicates that the compound was active at this concentration but not tested at lower doses.

TABLE A

| EXAMPLE | IC50 (µM) |     | EXAMPLE | IC50 (µM) |     |
| --- | --- | --- | --- | --- | --- |
| 50  | 0.2      |     | 56  | $\leq 1.0$ |     |
| 57  | $\leq 1.0$ | (1) | 58  | 0.004    |     |
| 62  | 1.9      |     | 65  | 3.8      |     |
| 66  | $\leq 1.0$ |     | 94  | $\leq 1.0$ | (1) |
| 72  | 0.03     |     | 82  | $\leq 1.0$ |     |
| 85  | 0.6      |     | 86  | 2.6      |     |
| 87  | 8.0      |     | 90  | 2.2      |     |
| 91  | 0.1      |     | 93  | 1.1      |     |
| 95  | 2.8      |     | 96  | 0.01     |     |
| 97  | 2.3      |     | 98  | 0.3      |     |
| 102 | 5.2      |     | 103 | 1.9      |     |
| 104 | $\leq 1.0$ |     | 105 | $\leq 1.0$ |     |
| 106 | 0.5      |     | 107 | $\leq 0.01$ |     |
| 108 | 1.2      |     | 109 | 3.6      |     |
| 110 | 0.2      |     | 111 | 7.3      |     |
| 112 | 3.0      |     | 113 | 0.3      |     |
| 114 | 4.2      |     | 115 | 1.2      |     |
| 116 | 2.0      |     | 117 | 0.2      |     |
| 118 | 1.4      |     | 119 | 2.4      |     |
| 120 | 4.2      |     | 121 | $\leq 1.0$ |     |
| 122 | 2.8      |     | 123 | 0.7      |     |
| 125 | 2.2      |     | 126 | 3.7      |     |
| 127 | 1.9      |     | 128 | 2.0      |     |
| 129 | 2.1      |     |     |          |     |

Notes
(1) Active in one test at 10 µM and active in one test at 1 µM.

Preferred compounds of the present invention are active in an in-vivo test which determines the ability of the compounds to inhibit the release of tumour necrosis factor-α (TNF-α) in a mouse endotoxin shock model (Test B). This model is similar to that described by Zuckerman and Bendele (1989), Infection and Immunity 57 (10): p3009–3013.

Test B (Mouse Tumour Necrosis Factor Test) was carried out in the following manner:

Each compound of formula I was combined with a carrier of a solution of 1.5% v/v sorbitan esters under the trade name Tween 80 and 0.25% v/v cellosize in sterile water (100 µl) and was administered orally to a group of four BALB/c mice. The concentration of compound was such as to provide dosages selected from 100, 30, 10, 3, 1, 0.1 and 0.03 mg/kg. Two hours after such oral administration, lipopolysaccharide (LPS) (E. coli 0127:B8) (100 μg) in sterile water (0.2 ml) was administered intraperitoneally to the test mice.

A control group of eight BALB/c mice was treated in a similar manner as the test group except that no test compound was included with the carrier.

One hour after LPS administration the mice were killed and blood was collected by cardiac puncture. The blood was incubated at 20° C. for 2 hours and the serum was separated from the clotted blood following centrifugation. Serum tumour necrosis factor-α (TNF-α) levels were assayed by an enzyme-linked immunosorbent assay (ELISA) and the concentration of TNF-α in each of the drug-treated groups was compared with the control group by one-way analysis of variance followed by a multiple t-test.

The ELISA was carried out by coating a 96-well vinyl assay plate (Costar) overnight at 4° C. with 50 μl per well of 2 μg/ml hamster anti-mouse TNF monoclonal antibody in 0.1M sodium hydrogen carbonate buffer at pH 8.2. After washing the plate with phosphate buffered saline (PBS) containing 0.05% v/v sorbitan esters under the trade name Tween 20 (wash buffer), a blocking/dilution buffer (10% sheep serum in PBS containing 0.1% v/v sorbitan esters under the trade name Tween 20 (200 μl)) was aliquoted to each well and incubated at 37° C. for 0.5 hours. After aspirating the blocking buffer, the serum samples and pure TNF (as a standard) diluted in blocking/dilution buffer, were added to the wells and incubated at 37° C. for 2 hours. After washing with the wash buffer, a polyclonal rabbit anti-mouse TNF-α antibody in blocking/dilution buffer (100 μl of a 1 in 10,000 dilution) was added and incubated for a further 1.5 hours at 37° C. After further washes, anti-rabbit IgG peroxidase conjugate (100 μl of a 1 in 4000 dilution) was added and incubated at 37° C. for 0.5 hours. After further washing, the substrate solution (100 μl per well of 0.1 mg/ml 3,3', 5,5'-tetramethylbenzidine dihydrochloride in 0.1M phosphate citrate buffer, pH 5.0, to which 2 μl of 30% hydrogen peroxide per 10 ml was added just before use) was added and the colour allowed to develop. The reaction was stopped by the addition of 1M sulphuric acid (25 μl) and the optical density read in a multichannel spectrophotometer at 450 nm. The mean TNF-α concentration was determined by comparison with the standard curve and the mean TNF-α concentration for each group compared with that produced by the control group. Drug treatments which cause a statistically significant reduction in TNF-α concentration of $\geq 35\%$ at a single dose at 100 mg/kg or less were considered active.

Table B below lists compounds of formula I deemed to be active in Test B. The lowest dose (minimum effective dose [MED]) for which activity was found is given in Table B. The symbol $\leq$ indicates that the compound was active at the dose given but not tested at lower doses.

TABLE B

| EXAMPLE | MTNF:MED (mg/kg) | EXAMPLE | MTNF:MED (mg/kg) |
|---|---|---|---|
| 52 | 100 | 53 | 30 |
| 57 | 100 | 86 | ≦10 |
| 87 | ≦100 | 88 | ≦30 |
| 89 | ≦30 | 90 | ≦30 |
| 91 | 30 | 93 | 30 |
| 95 | ≦3 | 98 | 30 |
| 99 | 100 | 100 | 100 |
| 101 | 100 | 102 | ≦100 |
| 103 | ≦30 | 104 | ≦100 |

TABLE B-continued

| EXAMPLE | MTNF:MED (mg/kg) | EXAMPLE | MTNF:MED (mg/kg) |
|---|---|---|---|
| 109 | 100 | 111 | ≦10 |
| 112 | 100 | 113 | 10 |
| 114 | 30 | 115 | 100 |
| 116 | 30 | 117 | 100 |
| 118 | ≦100 | 121 | 100 |
| 122 | ≦30 | 123 | ≦30 |
| 124 | ≦30 | 125 | 30 |
| 126 | ≦100 | 127 | 30 |
| 128 | ≦30 | 129 | 30 |
| 92 | ≦10 | | |

Some compounds have also been found to be active in a test which determines the magnitude of a cell mediated immune response in-vivo (Rat GvH test) (Test C). Test C is developed from the lymph node weight assay of Ford, Burr and Simonson, Transplantation 1970; 10: 258–266 in which parental strain spleen cells were injected into the feet of $F_1$ hybrid recipients and has been used to determine the ability of test compounds to inhibit a graft versus host (GvH) response in rats.

Test C (Rat GvH test) was carried out in the following manner:

Female DA rats of 6 to 8 weeks of age were killed using a rising concentration of $CO_2$. The spleens were removed and teased using a scalpel and forceps to produce a single cell suspension in Hanks balanced salt solution (HBSS). The suspension was filtered through a cell strainer (Falcon), sedimented by centrifugation and resuspended in 2 ml Tris ammonium chloride pH 7.2 (medium D from Test A) per spleen to lyse the erythrocytes. The cell suspension was sedimented again, resuspended in HBSS and filtered. The cells were washed twice more by centrifugation and resuspension in HBSS and finally resuspended in HBSS at a concentration of $3 \times 10^8$ cells/ml. 0.1 ml of this suspension was injected into the right hind footpad of groups of 4 female $(DA \times LEW)F_1$ rats. The left hind footpads were injected with HBSS as a control. Test compounds were administered daily to the rats orally as a solution or suspension in water containing 1.5% Tween 80 and 0.25% cellosize from day 0 to 6 inclusive. On day 7 the popliteal lymph nodes were dissected out and weighed. The dosages used were selected from the following values: 50, 30, 10, 3, 1, 0.3 or 0.1 mg/kg. The GvH response was determined by the difference in weight between the left and right hind popliteal nodes.

Rat GvH data were expressed as the mean percentage inhibition of popliteal node weight increase caused by the test compound calculated by the following equation:

$$\% \text{ inhibition} = 100 - \frac{\text{test} \times 100}{\text{control}}$$

where:
control=mean difference in left and right hind popliteal node weights in the group treated with the vehicle only,
test=mean difference in left and right hind popliteal lymph node weights in the group treated with the test compound.

Compounds were considered active in this test if they produced a 25% or greater inhibition of the lymph node weight increase, compared with that obtained in the group treated only with vehicle, in at least two out of three tests. Statistical significance was assessed using Dunnett's test (p<0.05).

Table C below lists the Example Number of compounds of formula I which were deemed to be active in Test C at 50 mg/kg following oral administration.

TABLE C

| Example | | |
|---|---|---|
| 98 | 110 | 114 |
| 117 | 119 | 123 |
| 93 | | |

Thus, the compounds of the present invention also show activity in in-vivo screens, which show the utility of the compounds as immunomodulants, particularly in suppressing the immune response. The compounds of the invention may show therapeutic activity in mammals at a dose of 200 mg/kg or lower. Preferred compounds of the invention show activity at 100 mg/kg or lower.

The compounds of formula I may also be antiinflammatory agents and may show therapeutic activity at a dose of 200 mg/kg or lower in standard laboratory animals. The therapeutic activity of compounds of formula I has been demonstrated by one or both of the following tests D and E.

Test D was carried out in the following way:
Inhibition of Arachidonic Acid Release from Zymosan Stimulated Macrophages Female MF1 mice (weighing 20 to 25 g) were killed using a rising concentration of $CO_2$. The mice were laid on their backs and the abdomens wiped with 70% alcohol. The skin was pulled back, exposing the peritoneal wall. Medium A (5 ml) (see below) was injected into the peritoneal cavity of each mouse followed by approximately 1 ml of air using a 20 ml syringe and a 21G×40 mm needle in order to form a suspension of macrophage cells. The medium and cells were then removed using a 19G×40 mm needle. The resulting suspension was returned to a sterile beaker kept on ice. The extracts from all the mice were pooled and this pooled cell suspension was counted using a Coulter counter and adjusted to a final cell count of 1–1.333 $10^6$ cells/ml prior to labelling with [$^3$H]-arachidonic acid. Typically five mice provided sufficient cells for each multiwell plate.

Sufficient [$^3$H]arachidonic acid in ethanol to give a final concentration of 1.6 µCi/ml (equivalent to 40 µCi/plate) was blown to dryness under nitrogen. The arachidonic acid was then resuspended in 1 or 2 ml of the cell suspension which was then mixed with the remainder of the cell suspension in a centrifuge bottle. The labelled cell suspension was then plated out into sterile plastic 96 flat-bottomed well plates (250 µl per well) and incubated overnight at 37° C. in a moist atmosphere of 5% $CO_2$, 95% air.

The following day, non-adherent cells were removed by washing 3 times with sterile phosphate buffered saline (PBS). The adherent peritoneal macrophages were then cultured for a further 24 hours in the presence or absence of drugs, in medium B (see below) at 37° in a 5% $CO_2$ atmosphere in order to measure the effects of drugs on the spontaneous release of arachidonic acid in the absence of stimulus. After this incubation, supernatants were removed to give media 1 and stored in sealed multi-well plates at 4° C. prior to scintillation counting. Drugs which potentiated spontaneous release of arachidonic acid (125% of controls) were deemed to be toxic at the concentration at which this phenomenon occurred. The supernatants were replaced by fresh medium C containing fresh drug and a stimulus. Three drugs were tested at six concentrations (100, 50, 20, 10, 5 and 1 µM) in replicates of four on each plate. The other wells contained controls consisting of a positive control (e.g. dexamethasone), medium (B) only and medium C only.

Incubation was then continued for a further 5 hours, whereupon the supernatants were collected to give media 2 and the adherent cells washed with PBS. The cells were then lysed with 100 µl of 0.1% TRITON® X100 in a 0.1% solution of bovine serum albumin in 0.9% saline and mechanically disrupted to give cell lysates. These supernatants (media 2) and cell lysates (Cells) were also stored in sealed multi-well plates at 4° C. prior to scintillation counting. 200 µl aliquots of media, or 100 µl aliquots of cells were counted using 2 ml of OPTIPHASE "HIGH SAFE" (Trademark of LKB) as scintillant.

Calculation of results

The percentage of arachidonic acid released was calculated using the mean values for each group of 4 wells in the following equation.

$$\% \text{ Release} = \frac{cpm \text{ in media } 2}{cpm \text{ in media } 2 + cpm \text{ in cell lysate}} \times 100$$

The value for the arachidonic acid release in the absence of stimulus (spontaneous, cpm of media 2) from cells which had been exposed to neither stimulus nor drug was subtracted from all equivalent values (cpm media 2, stimulated with or without drug) to give the net stimulated release. The percentage inhibition of arachidonic acid release caused by a drug may then be calculated using the following equation.

$$\% \text{ inhibition} = 100 - \frac{\text{net stimulated release in presence of drug} \times 100}{\text{net stimulated release in absence of drug}}$$

Compounds of formula I were tested at six concentrations (100, 50, 20, 10, 5 and 1 µM) and $IC_{50}$ values calculated. Compounds with IC50 values <100 µM are considered to be active. Advantageous compounds have an IC50 value <50 µM.

Medium A (for peritoneal lavage)

To a sterile 100 ml measuring cylinder was added: 40 ml $TC_{199}$ with Earle's salts (ten-fold concentrate) (ICN); 4 ml heat inactivated swine serum (ICN); 10 ml sodium bicarbonate (7.5% in sterile water); 0.4 ml antibiotics solution (60 mg/ml benzylpenicillin+100 mg/ml streptomycin) and 0.72 ml heparin (5000 U/ml). This mixture was transferred to sterile flask and made up to 400 ml with sterile water.

Medium B (for cell culture)

To a sterile 250 ml measuring cylinder was added: 65 ml TC 199 (ten-fold concentrate) with Earle's salts (ICN); 6.5 ml heat inactivated swine serum; 16.25 ml sodium bicarbonate (7.5% in sterile water); 0.65 ml antibiotics solution as above and 65 mg glutamine. This mixture was transferred to a sterile beaker and made up to 650 ml with sterile water.

Medium C=medium B+stimulant (zymosan)

The zymosan stimulant was prepared as follows: zymosan (200 mg) (supplied by Sigma) was added to PBS (20 ml). The mixture was boiled for 30 minutes and the volume restored to 20 ml with water. The zymosan was harvested by centrifugation at 500×g for 5 minutes, washed twice by resuspension in PBS (10 ml) and centrifugation. After the final separation, the zymosan was resuspended in 20 ml PBS and stored as 1 ml aliquots at −20° C. 650 ml medium B containing 15 ml zymosan=12.5 particles per cell was made up and then stored in 3 ml aliquots in a freezer.

As stated above, compounds with $IC_{50}$ values $\leq 100$ µm were considered to be active.

Table D below lists the Example Number of compounds of formula I deemed to be active in Test D. The final concentration of test compound which causes 50% inhibition of the immune response (IC50) for each compound is given in Table D.

TABLE D

| EXAMPLE | IC50 (μM) | EXAMPLE | IC50 (μM) |
|---|---|---|---|
| 87 | 18 | 88 | 52 |
| 90 | 31 | 91 | 17 |
| 93 | 56 | 96 | 34 |
| 98 | 62 | 99 | 58 |
| 100 | 27 | 101 | 18 |
| 102 | 54 | 103 | 28 |
| 106 | 22 | 107 | 22 |
| 109 | 14 | 110 | 20 |
| 112 | 16 | 113 | 33 |
| 114 | 34 | 115 | 31 |
| 116 | 18 | 117 | 21 |
| 120 | 100 | 122 | 52 |
| 123 | 35 | 127 | 16 |
| 128 | 27 | 129 | 16 |

Test E was carried out in the following way:
Carrageenan-induced rat paw oedema test Female rats, weight range 125–150 g were fasted overnight. One of the hind legs of each animal was marked with a line at the connection between the cuboid/navicular and calcaneus/talus bones. Groups of six rats were orally dosed at 10 ml/kg, in random order, with a given dose of the test compound given as a solution or suspension in 10% (w/v) aqueous acacia solution.

One hour after dosing, 0.1 ml of 1% (w/v) sterile carrageenan λ in normal saline was injected deeply into the plantar surface of the marked hind foot of each rat. The volume of the foot (up to the marked line) was measured immediately after injection using duplicate water displacement readings. Three hours after injection the foot volume was measured again and the percentage increase in foot volume relative to the initial reading was calculated.

The increase in foot volume (i.e. the degree of oedema) in drug treated animals when compared with that in the drug untreated control gave the degree of inhibition of paw oedema by the drug.

Compounds were considered to be active in this test if they produced a 20% or greater inhibition of paw oedema in at least two out of three tests after oral dosing at 100 mg/kg. Statistical significance was assessed using the Student's t test for single dose studies and Dunnett's test for multiple dose studies. More advantageous compounds were active in both Tests D and E.

Examples 87, 93 and 98 were deemed to be active in Test E.

We claim:

1. A compound of formula I

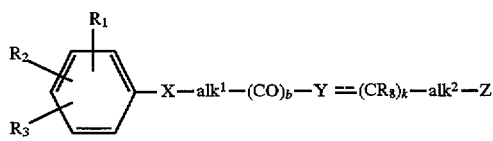

or a pharmaceutically acceptable salt thereof, in which $R_1$ and $R_3$ are both hydrogen and $R_2$ is hydrogen, halo, trifluoromethyl, $C_{1-6}$ alkyl, $C_{1-6}$ alkoxy or $C_{1-6}$ alkylthio, or $R_2$ and $R_3$ are both hydrogen and $R_1$ together with X and the phenyl group to which they are attached form a tetrahydronaphthyl group;

X is a bond, b is 0 or 1 and $alk^1$ is $C_{1-4}$ alkylene;

Y is a member selected from the group consisting of III(a), III(b), III(c), and III(e):

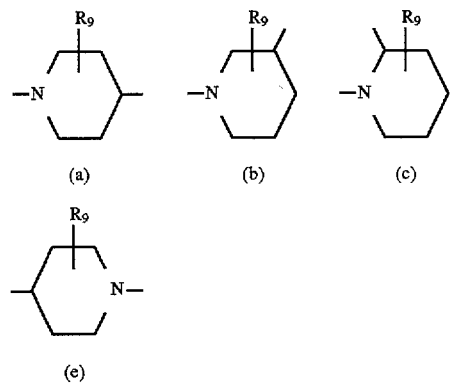

in which $R_9$ is hydrogen, $C_{1-6}$ alkyl, hydroxy-(C1-6)alkyl or $(C_{1-6})$alkoxy$(C_{1-6})$alkyl;

$R_8$ is hydrogen or $C_{1-4}$ alkyl;

k is 0 or 1 provided that when k is 1, $CR_8$ is linked to a carbon atom in the group Y;

the dotted line in – – –,
(a) represents a bond when k is 1;
(b) does not represent a bond when k is 0;

$alk^2$ is a $C_{1-6}$ alkylene chain optionally substituted by one or more $C_{1-4}$ alkyl groups;

Z is imidazol-1-yl, 1,2,4-triazol-1-yl, 1,2,3-triazol-1-yl, 1,2,3-triazol-2-yl, tetrazol-2-yl or benzimidazol-1-yl, each of which is optionally substituted by one to three groups selected from halo, trifluoromethyl, $C_{1-12}$alkyl, phenyl and benzoyl, said phenyl or benzoyl groups being optionally substituted by halo;

provided that;

when k is 0 and Y is connected to $alk^2$ through a nitrogen atom, then $alk^2$ is not methylene.

2. A compound according to claim 1 in which Y is represented by group IIIa or IIIb and $R_9$ is hydrogen or methyl.

3. A compound according to claim 1 in which b is 0.

4. A compound according to claim 1 in which k is 0.

5. A compound according to claim 1 in which $alk^1$ and $alk^2$ are both $C_{2-4}$ alkylene.

6. A compound according to claim 1 selected from:

the group consisting of
4-[2-(Imidazol-1-yl)ethyl]-1-(3-phenylpropyl) piperidine and
3-Imidazol-1-ylmethyl-1-(3-phenylpropionyl) piperidine.

7. A pharmaceutical composition comprising a compound of formula I as defined in claim 1 or a pharmaceutically acceptable salt thereof, together with a pharmaceutically acceptable carrier.

8. A method of treating inflammatory and/or allergic conditions in a mammal in need of such treatment comprising the administration of a therapeutically effective amount of a compound of formula I according to said mammal.

9. A process for preparing the compound of formula I as defined in claim 1, wherein Y is a group IIa

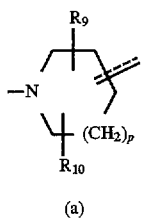

(a)

where p is 1, and $R_9$ and $R_{10}$ independently are hydrogen, $C_{1-6}$alkyl, hydroxy($C_{1-6}$)alkyl or $C_{1-6}$ alkoxy($C_{1-6}$)alkyl, comprising reacting a compound of formula VIII

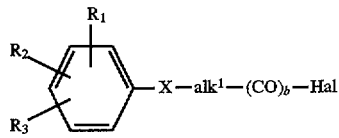

in which Hal is halo and $R_1$, $R_2$, $R_3$, X, $alk^1$ and b are as defined in claim 1, with a compound of formula IX

in which Y is a group IIa, $R_9$, $R_{10}$ and p are as hereinabove defined, and $R_8$, k, $alk^2$ and Z are as defined in claim 1.

10. A method of suppressing the immune system in a mammal in need of such treatment comprising administering a therapeutically effective amount of a compound formula I according to claim 1 to said mammal.

11. A compound represented by formula VII

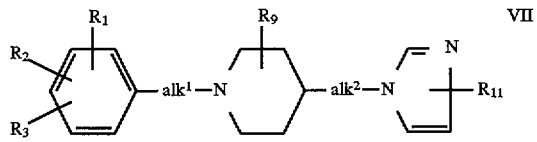

in which $R_1$ and $R_3$ represent hydrogen and $R_2$ is hydrogen, chloro, trifluoromethyl, methyl, methoxy or methylthio;

$alk^1$ and $alk^2$ represent $C_{2-4}$alkylene;

$R_9$ is hydrogen or methyl; and $R_{11}$ is hydrogen, halo, trifluoromethyl, $C_{1-12}$alkyl, phenyl or benzoyl, said phenyl or benzoyl groups being optionally substituted by halo.

* * * * *

UNITED STATES PATENT AND TRADEMARK OFFICE
CERTIFICATE OF CORRECTION

PATENT NO.: 5,741,800

DATED: April 21, 1998

INVENTOR(S): WEBBER et al.

It is certified that error appears in the above-identified patent and that said Letters Patent is hereby corrected as shown below:

On the title page, delete "[22] Filed: Dec. 21, 1995" and insert the following PCT data:

--[22] PCT Filed: Jun. 10, 1994
 [86] PCT No.: PCT/EP 94/01925
 § 371 Date: Dec. 21, 1995
 § 102 Date: Dec. 21, 1995
 [87] PCT Pub. No. WO95/00507
 PCT Pub. Date: Jan. 5, 1995--

Col. 50, claim 1, line 17, "(C1-6)" should be --($C_{1-6}$)--.

Signed and Sealed this

Eighteenth Day of August, 1998

Attest:

BRUCE LEHMAN

*Attesting Officer*   *Commissioner of Patents and Trademarks*